US008912207B2

(12) United States Patent
Boebel et al.

(10) Patent No.: US 8,912,207 B2
(45) Date of Patent: Dec. 16, 2014

(54) 2-ALDOXIMINO-5-FLUOROPYRIMIDINE DERIVATIVES

(75) Inventors: Timothy A. Boebel, Indianopolis, IN (US); Beth Lorsbach, Indianapolis, IN (US); Timothy P. Martin, Noblesville, IN (US); W. John Owen, Carmel, IN (US); Michael T. Sullenberger, Westfield, IN (US); Chenglin Yao, Westfield, IN (US)

(73) Assignee: Dow AgroSciences, LLP., Indianapolis, IN (US)

( * ) Notice: Subject to any disclaimer, the term of this patent is extended or adjusted under 35 U.S.C. 154(b) by 182 days.

(21) Appl. No.: 12/970,437

(22) Filed: Dec. 16, 2010

(65) Prior Publication Data

US 2011/0152300 A1    Jun. 23, 2011

Related U.S. Application Data

(60) Provisional application No. 61/287,346, filed on Dec. 17, 2009.

(51) Int. Cl.
*A01N 43/54* (2006.01)
*C07D 239/47* (2006.01)

(52) U.S. Cl.
CPC .............. *C07D 239/47* (2013.01); *A01N 43/54* (2013.01)
USPC .......................................... 514/274; 544/317

(58) Field of Classification Search
CPC ............................... C07D 239/47; A01N 43/54
USPC .......................................... 544/317; 514/274
See application file for complete search history.

(56) References Cited

U.S. PATENT DOCUMENTS

2009/0203647 A1*   8/2009   Benko et al. ................... 514/86

FOREIGN PATENT DOCUMENTS

| JP | H045279 | 1/1992 |
| WO | WO 03/043993 | 5/2003 |
| WO | WO2005079798 A1 | 9/2005 |

OTHER PUBLICATIONS

European Patent Office, Extended European Search Report for Application No. 10842907, dated Apr. 19, 2013, 5 pages.
International Searching Authority, International Search Report for Application No. PCT/US2010/060792, dated Apr. 22, 2011, 2 pages.
International Searching Authority, Written Opinion for Application No. PCT/US2010/060792, dated Apr. 22, 2011, 3 pages.
International Searching Authority, International Preliminary Report on Patentability for Application No. PCT/US2010/060792, dated Jun. 19, 2012, 4 pages.
Waring, MJ Defining optimum lipophilicity and molecular weight ranges for drug candidates—Molecular weight dependent lower logD limits based on permeability, Bioorganic and Medicinal Chemistry Letters, vol. 19, Issue 10, May 2009, pp. 2844-2851.
Dezhi Zhang, et al. Introduction of Pharmacy, China Medical Science and Technology Press, Mar. 31, 2008 pp. 356-359.

* cited by examiner

*Primary Examiner* — James O Wilson
*Assistant Examiner* — Ebenezer O Sackey
(74) *Attorney, Agent, or Firm* — CW Arnett; Faegre Baker Daniels, LLP

(57) ABSTRACT

This present disclosure is related to the field of 2-aldoximino-5-fluoropyrimidines and their derivatives and to the use of these compounds as fungicides.

10 Claims, No Drawings

2-ALDOXIMINO-5-FLUOROPYRIMIDINE DERIVATIVES

CROSS REFERENCE TO RELATED APPLICATIONS

This application claims the benefit of U.S. Provisional Patent Application Ser. No. 61/287,346 filed Dec. 17, 2009, which is expressly incorporated by reference herein.

BACKGROUND AND SUMMARY OF THE INVENTION

Fungicides are compounds, of natural or synthetic origin, which act to protect and/or cure plants against damage caused by agriculturally relevant fungi. Generally, no single fungicide is useful in all situations. Consequently, research is ongoing to produce fungicides that may have better performance, are easier to use, and cost less.

The present disclosure relates to 2-aldoximino-5-fluoropyrimidine compounds and their use as fungicides. The compounds of the present disclosure may offer protection against ascomycetes, basidiomycetes, deuteromycetes and oomycetes.

One embodiment of the present disclosure may include compounds of Formula I:

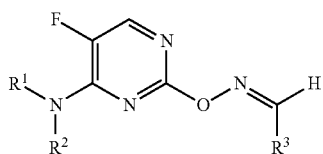

Formula I wherein $R^1$ is:
H;
$C_1$-$C_6$ alkyl optionally substituted with $R^4$;
$C_1$-$C_6$ alkenyl optionally substituted with $R^4$;
$C_3$-$C_6$ alkynyl optionally substituted with $R^4$;
phenyl or benzyl wherein each of the phenyl or the benzyl may be optionally substituted with 1-3 $R^5$, a 5- or 6-membered saturated or unsaturated ring containing 1-3 heteroatoms wherein each ring may be optionally substituted with 1-3 $R^5$;
—$(CHR^6)_m OR^7$;
—$C(=O)R^8$;
—$C(=S)R^8$;
—$C(=O)OR^8$;
—$C(=S)OR^8$;
—$(CHR^6)_m N(R^9)R^{10}$;
—$C(=O)N(R^9)R^{10}$; or
—$C(=S)N(R^9)R^{10}$;
m is an integer from 1 to 3;
$R^2$ is:
H; or
$C_1$-$C_6$ alkyl optionally substituted with $R^4$;
alternatively $R^1$ and $R^2$ may be taken together to form:
=$CR^{11}N(R^{12})R^{13}$;
$R^3$ is independently $C_1$-$C_6$ alkyl, $C_1$-$C_6$ cycloalkyl, $C_1$-$C_5$ haloalkyl, $C_2$-$C_6$ alkylcarbonyl, $C_2$-$C_6$ alkylaminocarbonyl, (hetero)arylcarbonyl, (hetero)aryloxycarbonyl, (hetero)arylaminocarbonyl, benzyl, phenyl, or 5- or 6-membered heteroaromatic ring, wherein each (hetero)aryl, phenyl, benzyl, or 5- or 6-membered heteroaromatic ring may be optionally substituted with 1 to 3 substituents independently selected from $R^5$;
$R^4$ is independently halogen, $C_1$-$C_6$ alkyl, $C_1$-$C_4$ haloalkyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_3$ alkylamino, $C_2$-$C_6$ alkoxycarbonyl, $C_2$-$C_6$ alkylcarbonyl, or $C_2$-$C_6$ alkylaminocarbonyl;
$R^5$ is independently halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, amino, $C_1$-$C_6$ alkylamino, $C_2$-$C_6$ dialkylamino, $C_2$-$C_6$ alkoxycarbonyl, or $C_2$-$C_6$ alkylcarbonyl, nitro, or cyano;
$R^6$ is H, $C_1$-$C_6$ alkyl, $C_1$-$C_6$ alkoxy, phenyl or benzyl wherein each of the phenyl or benzyl may be optionally substituted with 1 to 3 substituents independently selected from $R^5$;
$R^7$ is H, $C_1$-$C_6$ alkyl, $C_2$-$C_6$ alkenyl, $C_3$-$C_6$ alkynyl, $C_1$-$C_6$ haloalkyl, $C_1$-$C_6$ alkoxyalkyl, $C_2$-$C_6$ alkylcarbonyl, phenyl or benzyl wherein each of the phenyl or benzyl may be optionally substituted with 1 to 3 $R^5$, or a 5- or 6-membered saturated or unsaturated ring containing 1 to 3 heteroatoms wherein each ring may be optionally substituted with 1 to 3 substituents independently selected from $R^5$;
$R^8$ is H, $C_1$-$C_6$ alkyl, $C_2$-$C_6$ alkenyl, $C_3$-$C_6$ alkynyl, $C_1$-$C_6$ haloalkyl, $C_1$-$C_6$ alkoxyalkyl, phenyl or benzyl wherein each of the phenyl or the benzyl may be optionally substituted with 1 to 3 $R^5$, or a 5- or 6-membered saturated or unsaturated ring containing 1 to 3 heteroatoms wherein each ring may be optionally substituted with 1 to 3 substituents independently selected from $R^5$;
$R^9$ is H, $C_1$-$C_6$ alkyl, $C_1$-$C_6$ haloalkyl, $C_1$-$C_6$ alkoxyalkyl, $C_2$-$C_6$ alkylcarbonyl, phenyl or benzyl wherein each of the phenyl or the benzyl may be optionally substituted with 1-3 $R^5$, or a 5- or 6-membered saturated or unsaturated ring containing 1-3 heteroatoms wherein each ring may be optionally substituted with 1-3 $R^5$;
$R^{10}$ is H, $C_1$-$C_6$ alkyl, $C_1$-$C_6$ haloalkyl, $C_1$-$C_6$ alkoxyalkyl, $C_2$-$C_6$ alkylcarbonyl, benzyl, wherein the benzyl may be optionally substituted with 1-3 $R^5$
alternatively $R^9$ and $R^{10}$ may be taken together to form:
a 5- or 6-membered saturated or unsaturated ring containing 1-3 heteroatoms wherein each ring may be optionally substituted with 1-3 $R^5$;
$R^{11}$ is H or $C_1$-$C_4$ alkyl;
$R^{12}$ is H, $C_1$-$C_4$ alkyl, $C_1$-$C_6$ alkoxy, $C_2$-$C_6$, alkylcarbonyl, phenyl or benzyl wherein each of the phenyl or the benzyl may be optionally substituted with 1-3 $R^5$;
alternatively $R^{11}$ and $R^{12}$ may be taken together to form:
a 5- or 6-membered saturated or unsaturated ring containing 1-3 heteroatoms wherein each ring may be optionally substituted with 1-3 $R^5$;
$R^{13}$ is H, $C_1$-$C_4$ alkyl, $C_1$-$C_6$ alkoxy, $C_2$-$C_6$, alkylcarbonyl, phenyl or benzyl wherein each of the phenyl or the benzyl may be optionally substituted with 1-3 $R^5$;
alternatively $R^{12}$ and $R^{13}$ may be taken together to form:
a 5- or 6-membered saturated or unsaturated ring containing 1-3 heteroatoms wherein each ring may be optionally substituted with 1-3 $R^5$.

Another embodiment of the present disclosure may include a fungicidal composition for the control or prevention of fungal attack comprising the compounds described below and a phytologically acceptable carrier material.

Yet another embodiment of the present disclosure may include a method for the control or prevention of fungal attack on a plant, the method including the steps of applying a fungicidally effective amount of one or more of the compounds described below to at least one of the fungus, the plant, an area adjacent to the plant, and the seed adapted to produce the plant.

The term "alkyl" refers to a branched, unbranched, or cyclic carbon chain, including methyl, ethyl, propyl, butyl, isopropyl, isobutyl, tertiary butyl, pentyl, hexyl, cyclopropyl, cyclobutyl, cyclopentyl, cyclohexyl and the like.

The term "alkenyl" refers to a branched, unbranched or cyclic carbon chain containing one or more double bonds including ethenyl, propenyl, butenyl, isopropenyl, isobutenyl, cyclohexenyl, and the like.

The term "alkynyl" refers to a branched or unbranched carbon chain containing one or more triple bonds including propynyl, butynyl and the like.

As used throughout this specification, the term 'R' refers to the group consisting of $C_2$-$C_8$ alkyl, $C_3$-$C_8$ alkenyl, or $C_3$-$C_8$ alkynyl, unless stated otherwise.

The term "alkoxy" refers to an —OR substituent.

The term "alkoxycarbonyl" refers to a —C(O)—OR substituent.

The term "alkylcarbonyl" refers to a —C(O)—R substituent.

The term "alkylsulfonyl" refers to an —SO$_2$—R substituent.

The term "haloalkylsulfonyl" refers to an —SO$_2$—R substituent where R is fully or partially substituted with Cl, F, I, or Br or any combination thereof.

The term "alkylthio" refers to an —S—R substituent.

The term "haloalkylthio" refers to an alkylthio, which is substituted with Cl, F, I, or Br or any combination thereof.

The term "alkylaminocarbonyl" refers to a —C(O)—N(H)—R substituent.

The term "dialkylaminocarbonyl" refers to a —C(O)—NR$_2$ substituent.

The term "alkylcycloalkylamino" refers to a cycloalkylamino substituent that is substituted with an alkyl group.

The term "trialkylsilyl" refers to —SiR$_3$.

The term "cyano" refers to a —C≡N substituent.

The term "hydroxyl" refers to an —OH substituent.

The term "amino" refers to a —NH$_2$ substituent.

The term "alkylamino" refers to a —N(H)—R substituent.

The term "dialkylamino" refers to a —NR$_2$ substituent.

The term "alkoxyalkoxy" refers to —O(CH$_2$)$_n$O(CH$_2$)$_n$ where n is an integer from 1-3.

The term "alkoxyalkyl" refers to an alkoxy substitution on an alkyl.

The term "haloalkoxyalkyl" refers to an alkoxy substitution on an alkyl which may be partially substituted with Cl, F, Br, or I, or any combination thereof.

The term "hydroxyalkyl" refers to an alkyl which is substituted with a hydroxyl group.

The term "haloalkoxy" refers to an —OR—X substituent, wherein X is Cl, F, Br, or I, or any combination thereof.

The term "haloalkyl" refers to an alkyl, which is substituted with Cl, F, I, or Br or any combination thereof.

The term "haloalkenyl" refers to an alkenyl, which is substituted with Cl, F, I, or Br or any combination thereof.

The term "haloalkynyl" refers to an alkynyl which is substituted with Cl, F, I, or Br or any combination thereof.

The term "halogen" or "halo" refers to one or more halogen atoms, defined as F, Cl, Br, and I.

The term "hydroxycarbonyl" refers to a —C(O)—OH substituent.

The term "nitro" refers to a —NO$_2$ substituent.

Throughout the disclosure, reference to the compounds of Formula I is read as also including optical isomers and salts of Formula I, and hydrates thereof. Specifically, when Formula I contains a branched chain alkyl group, it is understood that such compounds include optical isomers and racemates thereof. Exemplary salts include: hydrochloride, hydrobromide, hydroiodide, and the like. Additionally, the compounds of Formula I may include tautomeric forms.

Certain compounds disclosed in this document can exist as one or more isomers. It will be appreciated by those skilled in the art that one isomer may be more active than the others. The structures disclosed in the present disclosure are drawn in only one geometric form for clarity, but are intended to represent all geometric and tautomeric forms of the molecule.

It is also understood by those skilled in the art that additional substitution is allowable, unless otherwise noted, as long as the rules of chemical bonding and strain energy are satisfied and the product still exhibits fungicidal activity.

Another embodiment of the present disclosure is a use of a compound of Formula I, for protection of a plant against attack by a phytopathogenic organism or the treatment of a plant infested by a phytopathogenic organism, comprising the application of a compound of Formula I, or a composition comprising the compound to soil, a plant, a part of a plant, foliage, and/or seeds.

Additionally, another embodiment of the present disclosure is a composition useful for protecting a plant against attack by a phytopathogenic organism and/or treatment of a plant infested by a phytopathogenic organism comprising a compound of Formula I and a phytologically acceptable carrier material.

Additional features and advantages of the present invention will become apparent to those skilled in the art upon consideration of the following detailed description of the illustrative embodiments exemplifying the best mode of carrying out the invention as presently perceived.

DETAILED DESCRIPTION OF THE PRESENT DISCLOSURE

The compounds of the present disclosure may be applied by any of a variety of known techniques, either as the compounds or as formulations comprising the compounds. For example, the compounds may be applied to the roots, seeds or foliage of plants for the control of various fungi, without damaging the commercial value of the plants. The materials may be applied in the form of any of the generally used formulation types, for example, as solutions, dusts, wettable powders, flowable concentrates, or emulsifiable concentrates.

Preferably, the compounds of the present disclosure are applied in the form of a formulation, comprising one or more of the compounds of Formula I with a phytologically acceptable carrier. Concentrated formulations may be dispersed in water, or other liquids, for application, or formulations may be dust-like or granular, which may then be applied without further treatment. The formulations can be prepared according to procedures that are conventional in the agricultural chemical art.

The present disclosure contemplates all vehicles by which one or more of the compounds may be formulated for delivery and use as a fungicide. Typically, formulations are applied as aqueous suspensions or emulsions. Such suspensions or emulsions may be produced from water-soluble, water suspendible, or emulsifiable formulations which are solids, usually known as wettable powders; or liquids, usually known as emulsifiable concentrates, aqueous suspensions, or suspension concentrates. As will be readily appreciated, any material to which these compounds may be added may be used, provided it yields the desired utility without significant interference with the activity of these compounds as antifungal agents.

Wettable powders, which may be compacted to form water dispersible granules, comprise an intimate mixture of one or more of the compounds of Formula I, an inert carrier and surfactants. The concentration of the compound in the wettable powder may be from about 10 percent to about 90 percent by weight based on the total weight of the wettable powder, more preferably about 25 weight percent to about 75 weight percent. In the preparation of wettable powder formulations, the compounds may be compounded with any finely divided solid, such as prophyllite, talc, chalk, gypsum, Fuller's earth, bentonite, attapulgite, starch, casein, gluten, montmorillonite clays, diatomaceous earths, purified silicates or the like. In such operations, the finely divided carrier and surfactants are typically blended with the compound(s) and milled.

Emulsifiable concentrates of the compounds of Formula I may comprise a convenient concentration, such as from about 10 weight percent to about 50 weight percent of the compound, in a suitable liquid, based on the total weight of the concentrate. The compounds may be dissolved in an inert carrier, which is either a water-miscible solvent or a mixture of water-immiscible organic solvents, and emulsifiers. The concentrates may be diluted with water and oil to form spray mixtures in the form of oil-in-water emulsions. Useful organic solvents include aromatics, especially the high-boiling naphthalenic and olefinic portions of petroleum such as heavy aromatic naphtha. Other organic solvents may also be used, for example, terpenic solvents, including rosin derivatives, aliphatic ketones, such as cyclohexanone, and complex alcohols, such as 2-ethoxyethanol.

Emulsifiers which may be advantageously employed herein may be readily determined by those skilled in the art and include various nonionic, anionic, cationic and amphoteric emulsifiers, or a blend of two or more emulsifiers. Examples of nonionic emulsifiers useful in preparing the emulsifiable concentrates include the polyalkylene glycol ethers and condensation products of alkyl and aryl phenols, aliphatic alcohols, aliphatic amines or fatty acids with ethylene oxide, propylene oxides such as the ethoxylated alkyl phenols and carboxylic esters solubilized with the polyol or polyoxyalkylene. Cationic emulsifiers include quaternary ammonium compounds and fatty amine salts. Anionic emulsifiers include the oil-soluble salts (e.g., calcium) of alkylaryl sulfonic acids, oil-soluble salts or sulfated polyglycol ethers and appropriate salts of phosphated polyglycol ether.

Representative organic liquids which may be employed in preparing the emulsifiable concentrates of the compounds of the present invention are the aromatic liquids such as xylene, propyl benzene fractions; or mixed naphthalene fractions, mineral oils, substituted aromatic organic liquids such as dioctyl phthalate; kerosene; dialkyl amides of various fatty acids, particularly the dimethyl amides of fatty glycols and glycol derivatives such as the n-butyl ether, ethyl ether or methyl ether of diethylene glycol, and the methyl ether of triethylene glycol and the like. Mixtures of two or more organic liquids may also be employed in the preparation of the emulsifiable concentrate. Organic liquids include xylene, and propyl benzene fractions, with xylene being most preferred in some cases. Surface-active dispersing agents are typically employed in liquid formulations and in an amount of from 0.1 to 20 percent by weight based on the combined weight of the dispersing agent with one or more of the compounds. The formulations can also contain other compatible additives, for example, plant growth regulators and other biologically active compounds used in agriculture.

Aqueous suspensions comprise suspensions of one or more water-insoluble compounds of Formula I, dispersed in an aqueous vehicle at a concentration in the range from about 5 to about 50 weight percent, based on the total weight of the aqueous suspension. Suspensions are prepared by finely grinding one or more of the compounds, and vigorously mixing the ground material into a vehicle comprised of water and surfactants chosen from the same types discussed above. Other components, such as inorganic salts and synthetic or natural gums, may also be added to increase the density and viscosity of the aqueous vehicle. It is often most effective to grind and mix at the same time by preparing the aqueous mixture and homogenizing it in an implement such as a sand mill, ball mill, or piston-type homogenizer.

The compounds of Formula I can also be applied as granular formulations, which are particularly useful for applications to the soil. Granular formulations generally contain from about 0.5 to about 10 weight percent, based on the total weight of the granular formulation of the compound(s), dispersed in an inert carrier which consists entirely or in large part of coarsely divided inert material such as attapulgite, bentonite, diatomite, clay or a similar inexpensive substance. Such formulations are usually prepared by dissolving the compounds in a suitable solvent and applying it to a granular carrier which has been preformed to the appropriate particle size, in the range of from about 0.5 to about 3 mm. A suitable solvent is a solvent in which the compound is substantially or completely soluble. Such formulations may also be prepared by making a dough or paste of the carrier and the compound and solvent, and crushing and drying to obtain the desired granular particle.

Dusts containing the compounds of Formula I may be prepared by intimately mixing one or more of the compounds in powdered form with a suitable dusty agricultural carrier, such as, for example, kaolin clay, ground volcanic rock, and the like. Dusts can suitably contain from about 1 to about 10 weight percent of the compounds, based on the total weight of the dust.

The formulations may additionally contain adjuvant surfactants to enhance deposition, wetting and penetration of the compounds onto the target crop and organism. These adjuvant surfactants may optionally be employed as a component of the formulation or as a tank mix. The amount of adjuvant surfactant will typically vary from 0.01 to 1.0 percent by volume, based on a spray-volume of water, preferably 0.05 to 0.5 volume percent. Suitable adjuvant surfactants include, but are not limited to ethoxylated nonyl phenols, ethoxylated synthetic or natural alcohols, salts of the esters or sulfosuccinic acids, ethoxylated organosilicones, ethoxylated fatty amines and blends of surfactants with mineral or vegetable oils. The formulations may also include oil-in-water emulsions such as those disclosed in U.S. patent application Ser. No. 11/495,228, the disclosure of which is expressly incorporated by reference herein.

The formulations may optionally include combinations that contain other pesticidal compounds. Such additional pesticidal compounds may be fungicides, insecticides, herbicides, nematocides, miticides, arthropodicides, bactericides or combinations thereof that are compatible with the compounds of the present invention in the medium selected for application, and not antagonistic to the activity of the present compounds. Accordingly, in such embodiments, the other pesticidal compound is employed as a supplemental toxicant for the same or for a different pesticidal use. The compounds of Formula I and the pesticidal compound in the combination can generally be present in a weight ratio of from 1:100 to 100:1.

The compounds of the present disclosure may also be combined with other fungicides to form fungicidal mixtures and synergistic mixtures thereof. The fungicidal compounds of the present disclosure are often applied in conjunction with one or more other fungicides to control a wider variety of undesirable diseases. When used in conjunction with other fungicide(s), the presently claimed compounds may be formulated with the other fungicide(s), tank mixed with the other fungicide(s) or applied sequentially with the other fungicide(s). Such other fungicides may include 2-(thiocyanatomethylthio)-benzothiazole, 2-phenylphenol, 8-hydroxyquinoline sulfate, ametoctradin, amisulbrom, antimycin, *Ampelomyces quisqualis*, azaconazole, azoxystrobin, *Bacillus subtilis*, *Bacillus subtilis* strain QST713, benalaxyl, benomyl, benthiavalicarb-isopropyl, benzylaminobenzene-sulfonate (BABS) salt, bicarbonates, biphenyl, bismerthiazol, bitertanol, bixafen, blasticidin-S, borax, Bordeaux mixture, boscalid, bromuconazole, bupirimate, calcium polysulfide, captafol, captan, carbendazim, carboxin, carpropamid, carvone, chlazafenone, chloroneb, chlorothalonil, chlozolinate, *Coniothyrium minitans*, copper hydroxide, copper octanoate, copper oxychloride, copper sulfate, copper sulfate (tribasic), cuprous oxide, cyazofamid, cyflufenamid, cymoxanil, cyproconazole, cyprodinil, dazomet, debacarb, diammonium ethylenebis-(dithiocarbamate), dichlofluanid, dichlorophen, diclocymet, diclomezine, dichloran, diethofencarb, difenoconazole, difenzoquat ion, diflumetorim, dimethomorph, dimoxystrobin, diniconazole, diniconazole-M, dinobuton, dinocap, diphenylamine, dithianon, dodemorph, dodemorph acetate, dodine, dodine free base, edifenphos, enestrobin, epoxiconazole, ethaboxam, ethoxyquin, etridiazole, famoxadone, fenamidone, fenarimol, fenbuconazole, fenfuram, fenhexamid, fenoxanil, fenpiclonil, fenpropidin, fenpropimorph, fenpyrazamine, fentin, fentin acetate, fentin hydroxide, ferbam, ferimzone, fluazinam, fludioxonil, flumorph, fluopicolide, fluopyram, fluoroimide, fluoxastrobin, fluquinconazole, flusilazole, flusulfamide, flutianil, flutolanil, flutriafol, fluxapyroxad, folpet, formaldehyde, fosetyl, fosetyl-aluminium, fuberidazole, furalaxyl, furametpyr, guazatine, guazatine acetates, GY-81, hexachlorobenzene, hexaconazole, hymexazol, imazalil, imazalil sulfate, imibenconazole, iminoctadine, iminoctadine triacetate, iminoctadine tris(albesilate), iodocarb, ipconazole, ipfenpyrazolone, iprobenfos, iprodione, iprovalicarb, isoprothiolane, isopyrazam, isotianil, kasugamycin, kasugamycin hydrochloride hydrate, kresoxim-methyl, laminarin, mancopper, mancozeb, mandipropamid, maneb, mepanipyrim, mepronil, mercuric chloride, mercuric oxide, mercurous chloride, metalaxyl, mefenoxam, meptyl-dinocap, metalaxyl-M, metam, metam-ammonium, metam-potassium, metam-sodium, metconazole, methasulfocarb, methyl iodide, methyl isothiocyanate, metiram, metominostrobin, metrafenone, mildiomycin, myclobutanil, nabam, nitrothal-isopropyl, nuarimol, octhilinone, ofurace, oleic acid (fatty acids), orysastrobin, oxadixyl, oxine-copper, oxpoconazole fumarate, oxycarboxin, pefurazoate, penconazole, pencycuron, penflufen, pentachlorophenol, pentachlorophenyl laurate, penthiopyrad, phenylmercury acetate, phosphonic acid, phthalide, picoxystrobin, polyoxin B, polyoxins, polyoxorim, potassium bicarbonate, potassium hydroxyquinoline sulfate, probenazole, prochloraz, procymidone, propamocarb, propamocarb hydrochloride, propiconazole, propineb, proquinazid, prothioconazole, pyraclostrobin, pyrametostrobin, pyraoxystrobin, pyrazophos, pyribencarb, pyributicarb, pyrifenox, pyrimethanil, pyriofenone, pyroquilon, quinoclamine, quinoxyfen, quintozene, *Reynoutria sachalinensis* extract, sedaxane, silthiofam, simeconazole, sodium 2-phenylphenoxide, sodium bicarbonate, sodium pentachlorophenoxide, spiroxamine, sulfur, SYP-Z071, SYP-Z048, tar oils, tebuconazole, tebufloquin, tecnazene, tetraconazole, thiabendazole, thifluzamide, thiophanate-methyl, thiram, tiadinil, tolclofos-methyl, tolylfluanid, triadimefon, triadimenol, triazoxide, tricyclazole, tridemorph, trifloxystrobin, triflumizole, triforine, tritiiconazole, validamycin, valifenalate, valiphenal, vinclozolin, zineb, ziram, zoxamide, *Candida oleophila, Fusarium oxysporum, Gliocladium* spp., *Phlebiopsis gigantea*, *Streptomyces griseoviridis, Trichoderma* spp., (RS)—N-(3,5-dichlorophenyl)-2-(methoxymethyl)-succinimide, 1,2-dichloropropane, 1,3-dichloro-1,1,3,3-tetrafluoroacetone hydrate, 1-chloro-2,4-dinitronaphthalene, 1-chloro-2-nitropropane, 2-(2-heptadecyl-2-imidazolin-1-yl)ethanol, 2,3-dihydro-5-phenyl-1,4-dithi-ine 1,1,4,4-tetraoxide, 2-methoxyethylmercury acetate, 2-methoxyethylmercury chloride, 2-methoxyethylmercury silicate, 3-(4-chlorophenyl)-5-methylrhodanine, 4-(2-nitroprop-1-enyl)phenyl thiocyanateme, ampropylfos, anilazine, azithiram, barium polysulfide, Bayer 32394, benodanil, benquinox, bentaluron, benzamacril; benzamacril-isobutyl, benzamorf, binapacryl, bis(methylmercury) sulfate, bis(tributyltin) oxide, buthiobate, cadmium calcium copper zinc chromate sulfate, carbamorph, CECA, chlobenthiazone, chloraniformethan, chlorfenazole, chlorquinox, climbazole, cyclafuramid, cypendazole, cyprofuram, decafentin, dichlone, dichlozoline, diclobutrazol, dimethirimol, dinocton, dinosulfon, dinoterbon, dipyrithione, ditalimfos, dodicin, drazoxolon, EBP, ESBP, etaconazole, etem, ethirim, fenaminosulf, fenapanil, fenitropan, 5-fluorocytosine and profungicides thereof, fluotrimazole, furcarbanil, furconazole, furconazole-cis, furmecyclox, furophanate, glyodine, griseofulvin, halacrinate, Hercules 3944, hexylthiofos, ICIA0858, isopamphos, isovaledione, mebenil, mecarbinzid, metazoxolon, methfuroxam, methylmercury dicyandiamide, metsulfovax, milneb, mucochloric anhydride, myclozolin, N-3,5-dichlorophenyl-succinimide, N-3-nitrophenylitaconimide, natamycin, N-ethylmercurio-4-toluenesulfonanilide, nickel bis(dimethyldithiocarbamate), OCH, phenylmercury dimethyldithiocarbamate, phenylmercury nitrate, phosdiphen, picolinamide UK-2A and derivatives thereof, prothiocarb; prothiocarb hydrochloride, pyracarbolid, pyridinitril, pyroxychlor, pyroxyfur, quinacetol; quinacetol sulfate, quinazamid, quinconazole, rabenzazole, salicylanilide, SSF-109, sultropen, tecoram, thiadifluor, thicyofen, thiochlorfenphim, thiophanate, thioquinox, tioxymid, triamiphos, triarimol, triazbutil, trichlamide, urbacid, and zarilamide, and any combinations thereof.

Additionally, the compounds of the present invention may be combined with other pesticides, including insecticides, nematocides, miticides, arthropodicides, bactericides or combinations thereof that are compatible with the compounds of the present invention in the medium selected for application, and not antagonistic to the activity of the present compounds to form pesticidal mixtures and synergistic mixtures thereof. The fungicidal compounds of the present disclosure may be applied in conjunction with one or more other pesticides to control a wider variety of undesirable pests. When used in conjunction with other pesticides, the presently claimed compounds may be formulated with the other pesticide(s), tank mixed with the other pesticide(s) or applied sequentially with the other pesticide(s). Typical insecticides include, but are not limited to: antibiotic insecticides such as allosamidin and thuringiensin; macrocyclic lactone insecticides such as spinosad and spinetoram; avermectin insecticides such as abamectin, doramectin, emamectin, eprinomectin, ivermectin and selamectin; milbemycin insecticides such as lepimectin, milbemectin, milbemycin oxime and moxidectin; arsenical insecticides such as calcium arsenate, copper acetoarsenite, copper arsenate, lead arsenate, potassium arsenite and sodium arsenite; botanical insecticides such as anabasine, azadirachtin, d-limonene, nicotine, pyrethrins, cinerins, cinerin I, cinerin II, jasmolin I, jasmolin II, pyrethrin I, pyrethrin II, quassia, rotenone, ryania and sabadilla; carbamate insecticides such as bendiocarb and carbaryl; benzofuranyl methylcarbamate insecticides such as benfuracarb, carbofuran, carbosulfan, decarbofuran and furathiocarb; dimethylcarbamate insecticides dimitan, dimetilan, hyquincarb and pirimicarb; oxime carbamate insecticides such as alanycarb, aldicarb, aldoxycarb, butocarboxim, butoxycarboxim, methomyl, nitrilacarb, oxamyl, tazimcarb, thiocarboxime, thiodicarb and thiofanox; phenyl methylcarbamate insecticides such as allyxycarb, aminocarb, bufencarb, butacarb, carbanolate, cloethocarb, dicresyl, dioxacarb, EMPC, ethiofencarb, fenethacarb, fenobucarb, isoprocarb, methiocarb, metolcarb, mexacarbate, promacyl, promecarb, propoxur, trimethacarb, XMC and xylylcarb; dessicant insecticides such as boric acid, diatomaceous earth and silica gel; diamide insecticides such as chlorantraniliprole, cyantraniliprole and flubendiamide; dinitrophenol insecticides such as dinex, dinoprop, dinosam and DNOC; fluorine insecticides such as barium hexafluorosilicate, cryolite, sodium fluoride, sodium hexafluorosilicate and sulfluramid; formamidine insecticides such as amitraz, chlordimeform, formetanate and formparanate; fumigant insecticides such as acrylonitrile, carbon disulfide, carbon tetrachloride, chloroform, chloropicrin, para-dichlorobenzene, 1,2-dichloropropane, ethyl formate, ethylene dibromide, ethylene dichloride, ethylene oxide, hydrogen cyanide, iodomethane, methyl bromide, methylchloroform, methylene chloride, naphthalene, phosphine, sulfuryl fluoride and tetrachloroethane; inorganic insecticides such as borax, calcium polysulfide, copper oleate, mercurous chloride, potassium thiocyanate and sodium thiocyanate; chitin synthesis inhibitors such as bistrifluoron, buprofezin, chlorfluazuron, cyromazine, diflubenzuron, flucycloxuron, flufenoxuron, hexaflumuron, lufenuron, novaluron, noviflumuron, penfluoron, teflubenzuron and triflumuron; juvenile hormone mimics such as epofenonane, fenoxycarb, hydroprene, kinoprene, methoprene, pyriproxyfen and triprene; juvenile hormones such as juvenile hormone I, juvenile hormone II and juvenile hormone III; moulting hormone agonists such as chromafenozide, halofenozide, methoxyfenozide and tebufenozide; moulting hormones such as α-ecdysone and ecdysterone; moulting inhibitors such as diofenolan; precocenes such as precocene I, precocene II and precocene III; unclassified insect growth regulators such as dicyclanil; nereistoxin analogue insecticides such as bensultap, cartap, thiocyclam and thiosultap; nicotinoid insecticides such as flonicamid; nitroguanidine insecticides such as clothianidin, dinotefuran, imidacloprid and thiamethoxam; nitromethylene insecticides such as nitenpyram and nithiazine; pyridylmethyl-amine insecticides such as acetamiprid, imidacloprid, nitenpyram and thiacloprid; organochlorine insecticides such as bromo-DDT, camphechlor, DDT, pp'-DDT, ethyl-DDD, HCH, gamma-HCH, lindane, methoxychlor, pentachlorophenol and TDE; cyclodiene insecticides such as aldrin, bromocyclen, chlorbicyclen, chlordane, chlordecone, dieldrin, dilor, endosulfan, alpha-endosulfan, endrin, HEOD, heptachlor, HHDN, isobenzan, isodrin, kelevan and mirex; organophosphate insecticides such as bromfenvinfos, chlorfenvinphos, crotoxyphos, dichlorvos, dicrotophos, dimethylvinphos, fospirate, heptenophos, methocrotophos, mevinphos, monocrotophos, naled, naftalofos, phosphamidon, propaphos, TEPP and tetrachlorvinphos; organothiophosphate insecticides such as dioxabenzolos, fosmethilan and phenthoate; aliphatic organothiophosphate insecticides such as acethion, amiton, cadusafos, chlorethoxyfos, chlormephos, demephion, demephion-O, demephion-S, demeton, demeton-O, demeton-S, demeton-methyl, demeton-O-methyl, demeton-S-methyl, demeton-S-methyl-sulphon, disulfoton, ethion, ethoprophos, IPSP, isothioate, malathion, methacrifos, oxydemeton-methyl, oxydeprofos, oxydisulfoton, phorate, sulfotep, terbufos and thiometon; aliphatic amide organothiophosphate insecticides such as amidithion, cyanthoate, dimethoate, ethoate-methyl, formothion, mecarbam, omethoate, prothoate, sophamide and vamidothion; oxime organothiophosphate insecticides such as chlorphoxim, phoxim and phoxim-methyl; heterocyclic organothiophosphate insecticides such as azamethiphos, coumaphos, coumithoate, dioxathion, endothion, menazon, morphothion, phosalone, pyraclofos, pyridaphenthion and quinothion; benzothiopyran organothiophosphate insecticides such as dithicrofos and thicrofos; benzotriazine organothiophosphate insecticides such as azinphos-ethyl and azinphos-methyl; isoindole organothiophosphate insecticides such as dialifos and phosmet; isoxazole organothiophosphate insecticides such as isoxathion and zolaprofos; pyrazolopyrimidine organothiophosphate insecticides such as chlorprazophos and pyrazophos; pyridine organothiophosphate insecticides such as chlorpyrifos and chlorpyrifos-methyl; pyrimidine organothiophosphate insecticides such as butathiofos, diazinon, etrimfos, lirimfos, pirimiphos-ethyl, pirimiphos-methyl, primidophos, pyrimitate and tebupirimfos; quinoxaline organothiophosphate insecticides such as quinalphos and quinalphos-methyl; thiadiazole organothiophosphate insecticides such as athidathion, lythidathion, methidathion and prothidathion; triazole organothiophosphate insecticides such as isazofos and triazophos; phenyl organothiophosphate insecticides such as azothoate, bromophos, bromophos-ethyl, carbophenothion, chlorthiophos, cyanophos, cythioate, dicapthon, dichlofenthion, etaphos, famphur, fenchlorphos, fenitrothion fensulfothion, fenthion, fenthion-ethyl, heterophos, jodfenphos, mesulfenfos, parathion, parathion-methyl, phenkapton, phosnichlor, profenofos, prothiofos, sulprofos, temephos, trichlormetaphos-3 and trifenofos; phosphonate insecticides such as butonate and trichlorfon; phosphonothioate insecticides such as mecarphon; phenyl ethylphosphonothioate insecticides such as fonofos and trichloronat; phenyl phenylphosphonothioate insecticides such as cyanofenphos, EPN and leptophos; phosphoramidate insecticides such as crufomate, fenamiphos, fosthietan, mephosfolan, phosfolan and pirimetaphos; phosphoramidothioate insecticides such as acephate, isocarbophos, isofenphos, isofenphos-methyl, methamidophos and propetamphos; phosphorodiamide insecticides such as dimefox, mazidox, mipafox and schradan; oxadiazine insecticides such as indoxacarb; oxadiazoline insecticides such as metoxadiazone; phthalimide insecticides such as dialifos, phosmet and tetramethrin; pyrazole insecticides such as tebufenpyrad, tolefenpyrad; phenylpyrazole insecticides such as acetoprole, ethiprole, fipronil, pyrafluprole, pyriprole and vaniliprole; pyrethroid ester insecticides such as acrinathrin, allethrin, bioallethrin, barthrin, bifenthrin, bioethanomethrin, cyclethrin, cycloprothrin, cyfluthrin, beta-cyfluthrin, cyhalothrin, gamma-cyhalothrin, lambda-cyhalothrin, cypermethrin, alpha-cypermethrin, beta-cypermethrin, theta-cypermethrin, zeta-cypermethrin, cyphenothrin, deltamethrin, dimefluthrin, dimethrin, empenthrin, fenfluthrin, fenpirithrin, fenpropathrin, fenvalerate, esfenvalerate, flucythrinate, fluvalinate, tau-fluvalinate, furethrin, imiprothrin, meperfluthrin, metofluthrin, permethrin, biopermethrin, transpermethrin, phenothrin, prallethrin, profluthrin, pyresmethrin, resmethrin, bioresmethrin, cismethrin, tefluthrin, terallethrin, tetramethrin, tetramethylfluthrin, tralomethrin and transfluthrin; pyrethroid ether insecticides such as etofenprox, flufenprox, halfenprox, protrifenbute and silafluofen; pyrimidinamine insecticides such as flufenerim and pyrimidifen; pyrrole insecticides such as chlorfenapyr; tetramic acid insecticides such as spirotetramat; tetronic acid insecticides such as spiromesifen; thiourea insecticides such as diafenthiuron; urea insecticides such as flucofuron and sulcofuron; and unclassified insecticides such as closantel, copper naphthenate, crotamiton, EXD, fenazaflor, fenoxacrim, hydramethylnon, isoprothiolane, malonoben, metaflumizone, nifluridide, plifenate, pyridaben, pyridalyl, pyrifluquinazon, rafoxanide, sulfoxaflor, triarathene and triazamate, and any combinations thereof.

Additionally, the compounds of the present invention may be combined with herbicides that are compatible with the compounds of the present invention in the medium selected for application, and not antagonistic to the activity of the present compounds to form pesticidal mixtures and synergistic mixtures thereof. The fungicidal compounds of the present disclosure may be applied in conjunction with one or more herbicides to control a wide variety of undesirable plants. When used in conjunction with herbicides, the presently claimed compounds may be formulated with the herbicide(s), tank mixed with the herbicide(s) or applied sequentially with the herbicide(s). Typical herbicides include, but are not limited to: amide herbicides such as allidochlor, beflubutamid, benzadox, benzipram, bromobutide, cafenstrole, CDEA, cyprazole, dimethenamid, dimethenamid-P, diphenamid, epronaz, etnipromid, fentrazamide, flupoxam, fomesafen, halosafen, isocarbamid, isoxaben, napropamide, naptalam, pethoxamid, propyzamide, quinonamid and tebutam; anilide herbicides such as chloranocryl, cisanilide, clomeprop, cypromid, diflufenican, etobenzanid, fenasulam, flufenacet, flufenican, mefenacet, mefluidide, metamifop, monalide, naproanilide, pentanochlor, picolinafen and propanil; arylalanine herbicides such as benzoylprop, flampropand flamprop-M; chloroacetanilide herbicides such as acetochlor, alachlor, butachlor, butenachlor, delachlor, diethatyl, dimethachlor, metazachlor, metolachlor, S-metolachlor, pretilachlor, propachlor, propisochlor, prynachlor, terbuchlor, thenylchlor and xylachlor; sulfonanilide herbicides such as benzofluor, perfluidone, pyrimisulfan and profluazol; sulfonamide herbicides such as asulam, carbasulam, fenasulam and oryzalin; thioamide herbicides such as chlorthiamid; antibiotic herbicides such as bilanafos; benzoic acid herbicides such as chloramben, dicamba, 2,3,6-TBA and tricamba; pyrimidinyloxybenzoic acid herbicides such as bispyribac and pyriminobac; pyrimidinylthiobenzoic acid herbicides such as pyrithiobac; phthalic acid herbicides such as chlorthal; picolinic acid herbicides such as aminopyralid, clopyralid and picloram; quinolinecarboxylic acid herbicides such as quinclorac and quinmerac; arsenical herbicides such as cacodylic acid, CMA, DSMA, hexaflurate, MAA, MAMA, MSMA, potassium arsenite and sodium arsenite; benzoylcyclohexanedione herbicides such as mesotrione, sulcotrione, tefuryltrione and tembotrione; benzofuranyl alkylsulfonate herbicides such as benfuresate and ethofumesate; benzothiazole herbicides such as benzazolin; carbamate herbicides such as asulam, carboxazole chlorprocarb, dichlormate, fenasulam, karbutilate and terbucarb; carbanilate herbicides such as barban, BCPC, carbasulam, carbetamide, CEPC, chlorbufam, chlorpropham, CPPC, desmedipham, phenisopham, phenmedipham, phenmedipham-ethyl, propham and swep; cyclohexene oxime herbicides such as alloxydim, butroxydim, clethodim, cloproxydim, cycloxydim, profoxydim, sethoxydim, tepraloxydim and tralkoxydim; cyclopropylisoxazole herbicides such as isoxachlortole and isoxaflutole; dicarboximide herbicides such as cinidon-ethyl, flumezin, flumiclorac, flumioxazin and flumipropyn; dinitroaniline herbicides such as benfluralin, butralin, dinitramine, ethalfluralin, fluchloralin, isopropalin, methalpropalin, nitralin, oryzalin, pendimethalin, prodiamine, profluralin and trifluralin; dinitrophenol herbicides such as dinofenate, dinoprop, dinosam, dinoseb, dinoterb, DNOC, etinofen and medinoterb; diphenyl ether herbicides such as ethoxyfen; nitrophenyl ether herbicides such as acifluorfen, aclonifen, bifenox, chlomethoxyfen, chlornitrofen, etnipromid, fluorodifen, fluoroglycofen, fluoronitrofen, fomesafen, furyloxyfen, halosafen, lactofen, nitrofen, nitrofluorfen and oxyfluorfen; dithiocarbamate herbicides such as dazomet and metam; halogenated aliphatic herbicides such as alorac, chloropon, dalapon, flupropanate, hexachloroacetone, iodomethane, methyl bromide, monochloroacetic acid, SMA and TCA; imidazolinone herbicides such as imazamethabenz, imazamox, imazapic, imazapyr, imazaquin and imazethapyr; inorganic herbicides such as ammonium sulfamate, borax, calcium chlorate, copper sulfate, ferrous sulfate, potassium azide, potassium cyanate, sodium azide, sodium chlorate and sulfuric acid; nitrile herbicides such as bromobonil, bromoxynil, chloroxynil, dichlobenil, iodobonil, ioxynil and pyraclonil; organophosphorus herbicides such as amiprofos-methyl, anilofos, bensulide, bilanafos, butamifos, 2,4-DEP, DMPA, EBEP, fosamine, glufosinate, glufosinate-P, glyphosate and piperophos; phenoxy herbicides such as bromofenoxim, clomeprop, 2,4-DEB, 2,4-DEP, difenopenten, disul, erbon, etnipromid, fenteracol and trifopsime; oxadiazoline herbicides such as methazole, oxadiargyl, oxadiazon; oxazole herbicides such as fenoxasulfone; phenoxyacetic herbicides such as 4-CPA, 2,4-D, 3,4-DA, MCPA, MCPA-thioethyl and 2,4,5-T; phenoxybutyric herbicides such as 4-CPB, 2,4-DB, 3,4-DB, MCPB and 2,4,5-TB; phenoxypropionic herbicides such as cloprop, 4-CPP, dichlorprop, dichlorprop-P, 3,4-DP, fenoprop, mecopropand mecoprop-P; aryloxyphenoxypropionic herbicides such as chlorazifop, clodinafop, clofop, cyhalofop, diclofop, fenoxaprop, fenoxaprop-P, fenthiaprop, fluazifop, fluazifop-P, haloxyfop, haloxyfop-P, isoxapyrifop, metamifop, propaquizafop, quizalofop, quizalofop-P and trifop; phenylenediamine herbicides such as dinitramine and prodiamine; pyrazole herbicides such as pyroxasulfone; benzoylpyrazole herbicides such as benzofenap, pyrasulfotole, pyrazolynate, pyrazoxyfen, and topramezone; phenylpyrazole herbicides such as fluazolate, nipyraclofen, pioxaden and pyraflufen; pyridazine herbicides such as credazine, pyridafol and pyridate; pyridazinone herbicides such as brompyrazon, chloridazon, dimidazon, flufenpyr, metflurazon, norflurazon, oxapyrazon and pydanon; pyridine herbicides such as aminopyralid, cliodinate, clopyralid, dithiopyr, fluoroxypyr, haloxydine, picloram, picolinafen, pyriclor, thiazopyr and triclopyr; pyrimidinediamine herbicides such as iprymidam and tioclorim; quaternary ammonium herbicides such as cyperquat, diethamquat, difenzoquat, diquat, morfamquat and paraquat; thiocarbamate herbicides such as butylate, cycloate, di-allate, EPTC, esprocarb, ethiolate, isopolinate, methiobencarb, molinate, orbencarb, pebulate, pro sulfocarb, pyributicarb, sulfallate, thiobencarb, tiocarbazil, tri-allate and vernolate; thiocarbonate herbicides such as dimexano, EXD and proxan; thiourea herbicides such as methiuron; triazine herbicides such as dipropetryn, indaziflam, triaziflam and trihydroxytriazine; chlorotriazine herbicides such as atrazine, chlorazine, cyanazine, cyprazine, eglinazine, ipazine, mesoprazine, procyazine, proglinazine, propazine, sebuthylazine, simazine, terbuthylazine and trietazine; methoxytriazine herbicides such as atraton, methometon, prometon, secbumeton, simeton and terbumeton; methylthiotriazine herbicides such as ametryn, aziprotryne, cyanatryn, desmetryn, dimethametryn, methoprotryne, prometryn, simetryn and terbutryn; triazinone herbicides such as ametridione, amibuzin, hexazinone, isomethiozin, metamitron and metribuzin; triazole herbicides such as amitrole, cafenstrole, epronaz and flupoxam; triazolone herbicides such as amicarbazone, bencarbazone, carfentrazone, flucarbazone, ipfencarbazone, propoxycarbazone, sulfentrazone and thiencarbazone-methyl; triazolopyrimidine herbicides such as cloransulam, diclosulam, florasulam, flumetsulam, metosulam, penoxsulam and pyroxsulam; uracil herbicides such as benzfendizone, bromacil, butafenacil, flupropacil, isocil, lenacil, saflufenacil and terbacil; urea herbicides such as benzthiazuron, cumyluron, cycluron, dichloralurea, diflufenzopyr, isonoruron, isouron, methabenzthiazuron, monisouron and noruron; phenylurea herbicides such as anisuron, buturon, chlorbromuron, chloreturon, chlorotoluron, chloroxuron, daimuron, difenoxuron, dimefuron, diuron, fenuron, fluometuron, fluothiuron, isoproturon, linuron, methiuron, methyldymron, metobenzuron, metobromuron, metoxuron, monolinuron, monuron, neburon, parafluoron, phenobenzuron, siduron, tetrafluoron and thidiazuron; pyrimidinylsulfonylurea herbicides such as amidosulfuron, azimsulfuron, bensulfuron, chlorimuron, cyclosulfamuron, ethoxysulfuron, flazasulfuron, flucetosulfuron, flupyrsulfuron, foramsulfuron, halosulfuron, imazosulfuron, mesosulfuron, metazosulfuron, nicosulfuron, orthosulfamuron, oxasulfuron, primisulfuron, propyrisulfuron, pyrazosulfuron, rimsulfuron, sulfometuron, sulfosulfuron and trifloxysulfuron; triazinylsulfonylurea herbicides such as chlorsulfuron, cinosulfuron, ethametsulfuron, iodosulfuron, metsulfuron, prosulfuron, thifensulfuron, triasulfuron, tribenuron, triflusulfuron and tritosulfuron; thiadiazolylurea herbicides such as buthiuron, ethidimuron, tebuthiuron, thiazafluoron and thidiazuron; and unclassified herbicides such as acrolein, allyl alcohol, aminocyclopyrachlor, azafenidin, bentazone, benzobicyclon, bicyclopyrone, buthidazole, calcium cyanamide, cambendichlor, chlorfenac, chlorfenprop, chlorflurazole, chlorflurenol, cinmethylin, clomazone, CPMF, cresol, cyanamide, ortho-dichlorobenzene, dimepiperate, endothal, fluoromidine, fluridone, fluorochloridone, flurtamone, fluthiacet, indanofan, methyl isothiocyanate, OCH, oxaziclomefone, pentachlorophenol, pentoxazone, phenylmercury acetate, prosulfalin, pyribenzoxim, pyriftalid, quinoclamine, rhodethanil, sulglycapin, thidiazimin, tridiphane, trimeturon, tripropindan and tritac.

Another embodiment of the present disclosure is a method for the control or prevention of fungal attack. This method comprises applying to the soil, plant, roots, foliage, seed or locus of the fungus, or to a locus in which the infestation is to be prevented (for example applying to cereal or grape plants), a fungicidally effective amount of one or more of the compounds of Formula I. The compounds are suitable for treatment of various plants at fungicidal levels, while exhibiting low phytotoxicity. The compounds may be useful both in a protectant and/or an eradicant fashion.

The compounds have been found to have significant fungicidal effect particularly for agricultural use. Many of the compounds are particularly effective for use with agricultural crops and horticultural plants. Additional benefits may include, but are not limited to, improving the health of a plant; improving the yield of a plant (e.g. increased biomass and/or increased content of valuable ingredients); improving the vigor of a plant (e.g. improved plant growth and/or greener leaves); improving the quality of a plant (e.g. improved content or composition of certain ingredients); and improving the tolerance to abiotic and/or biotic stress of the plant.

It will be understood by those in the art that the efficacy of the compound for the foregoing fungi establishes the general utility of the compounds as fungicides.

The compounds have broad ranges of activity against fungal pathogens. Exemplary pathogens may include, but are not limited to, wheat leaf blotch (*Septoria tritici*, also known as *Mycosphaerella graminicola*), apple scab (*Venturia inaequalis*), and *Cercospora* leaf spots of sugar beets (*Cercospora beticola*), leaf spots of peanut (*Cercospora arachidicola* and *Cercosporidium personatum*) and other crops, and black sigatoka of bananas (*Mycosphaerella fujiensis*). The exact amount of the active material to be applied is dependent not only on the specific active material being applied, but also on the particular action desired, the fungal species to be controlled, and the stage of growth thereof, as well as the part of the plant or other product to be contacted with the compound. Thus, all the compounds, and formulations containing the same, may not be equally effective at similar concentrations or against the same fungal species.

The compounds are effective in use with plants in a disease-inhibiting and phytologically acceptable amount. The term "disease-inhibiting and phytologically acceptable amount" refers to an amount of a compound that kills or inhibits the plant disease for which control is desired, but is not significantly toxic to the plant. This amount will generally be from about 0.1 to about 1000 ppm (parts per million), with 1 to 500 ppm being preferred. The exact amount of a compound required varies with the fungal disease to be controlled, the type of formulation employed, the method of application, the particular plant species, climate conditions, and the like. A suitable application rate is typically in the range from about 0.10 to about 4 pounds/acre (about 0.01 to 0.45 grams per square meter, g/m$^2$).

Any range or desired value given herein may be extended or altered without losing the effects sought, as is apparent to the skilled person for an understanding of the teachings herein.

The compounds of Formula I may be made using well-known chemical procedures. Intermediates not specifically mentioned in this disclosure are either commercially available, may be made by routes disclosed in the chemical literature, or may be readily synthesized from commercial starting materials utilizing standard procedures.

The following examples are presented to illustrate the various aspects of the compounds of the present disclosure and should not be construed as limitations to the claims.

Example 1

Preparation of N'-{5-fluoro-2-[1-phenylmethylidene-amino-oxy]pyrimidin-4-yl}-N,N-dimethylformamidine (1)

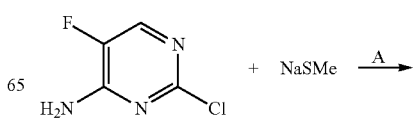

-continued

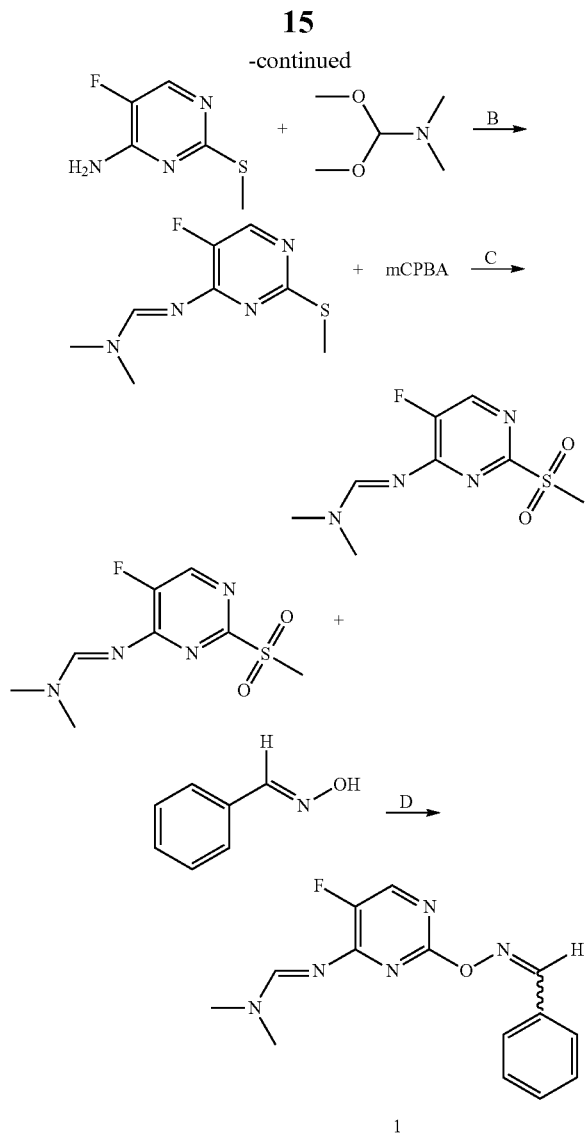

Step A. To a solution of 2-chloro-5-fluoropyrimidin-4-amine (15.50 grams (g), 105 millimoles (mmol)) in ethyl alcohol (EtOH; 420 milliliters (mL)) was added sodium thiomethoxide (NaSCH$_3$; 9.20 g, 131 mmol), and the resulting turbid mixture was warmed to reflux and stirred for 3 hours (h). The reaction mixture was cooled to room temperature, the solvent evaporated, and the residue partitioned between ethyl acetate (EtOAc; 250 mL) and water (H$_2$O; 250 mL). The phases were separated, and the aqueous phase was extracted with additional EtOAc (100 mL). The organic phases were combined, dried over sodium sulfate (Na$_2$SO$_4$), filtered, and concentrated to an off-white solid. The solid was purified by flash chromatography (330 g silica gel (SiO$_2$); 0→30% EtOAc/hexanes) to give 5-fluoro-2-methylsulfanylpyrimidin-4-ylamine (16.38 g, 98%) as a white solid: mp 114-115° C.; $^1$H NMR (400 MHz, CDCl$_3$) δ 7.99 (d, J=3.0 Hz, 1H), 5.29 (s, 2H), 2.50 (s, 3H); CIMS m/z 159 ([M]$^+$).

Step B. To a solution of 5-fluoro-2-methylsulfanylpyrimidin-4-ylamine (7.5 g, 47.1 mmol) in N,N-dimethylformamide (DMF; 18 mL) was added DMF-dimethylacetal (DMF-DMA; 8.42 g, 70.7 mmol), and the resulting solution was stirred under nitrogen (N$_2$) for 4 h. The homogeneous solution was diluted with diethyl ether (Et$_2$O; 500 mL), washed with H$_2$O (5×100 mL), and the organic phase was dried over Na$_2$SO$_4$, filtered, and concentrated to a white solid. Recrystallization from hexane afforded N'-(5-fluoro-2-methylsulfanylpyrimidin-4-yl)-N,N-dimethylformamidine (8.47 g, 84%) as white needles: mp 75-77° C.; $^1$H NMR (400 MHz, CDCl$_3$) δ 8.67 (s, 1H), 8.12 (d, J=3.1 Hz, 1H), 3.19 (s, 3H), 3.18 (s, 3H), 2.53 (s, 3H); CIMS m/z 214 ([M]$^+$).

Step C. To a solution of N'-(5-fluoro-2-methylsulfanylpyrimidin-4-yl)-N,N-dimethylformamidine (0.4 g, 1.87 mmol) in dichloromethane (CH$_2$Cl$_2$; 18 mL) was added m-chloroperoxybenzoic acid (mCPBA; 77%; 0.85 g, 3.92 mmol) at 0° C., and the resulting solution was warmed to room temperature and stirred under N$_2$ for 16 h. An additional portion of mCPBA (0.25 g) was added, and the solution was stirred for 3 h. The reaction was diluted with CH$_2$Cl$_2$ (50 mL) and washed with aqueous sodium bisulfite (200 mL of 10%), saturated aqueous sodium bicarbonate (NaHCO$_3$; 100 mL), and brine (100 mL), and the organic phase was dried over Na$_2$SO$_4$, filtered, and concentrated to a colorless oil. The oil was purified by flash chromatography (24 g SiO$_2$; 0→100% EtOAc/hexanes) to give N'-(5-fluoro-2-methanesulfonylpyrimidin-4-yl)-N,N-dimethylformamidine (0.14 g, 29%) as a white solid: mp 147-149° C.; $^1$H NMR (400 MHz, CDCl$_3$) δ 8.81 (s, 1H), 8.28 (d, J=2.6 Hz, 1H), 3.31 (s, 3H), 3.26 (s, 3H), 3.24 (s, 3H); CIMS m/z 246 ([M]$^+$).

Step D. To a suspension of sodium hydride (NaH, 60% dispersion in mineral oil; 0.037 g, 0.91 mmol) in DMF (2 mL) was added a solution of benzaldehyde oxime (0.125 g, 1.04 mmol) in DMF (1 mL), and the resulting frothy mixture was stirred for 1 h. To the resulting pale yellow mixture was added a solution of N'-(5-fluoro-2-methanesulfonylpyrimidin-4-yl)-N,N-dimethylformamidine (0.15 g, 0.61 mmol) in DMF (1 mL), and the homogeneous, pale-yellow solution was stirred at 25° C. for 16 h. The reaction mixture was diluted with H$_2$O (50 mL) and was extracted with CH$_2$Cl$_2$ (2×100 mL). The organic extracts were combined, washed with H$_2$O (5×50 mL) and brine (50 mL), dried over Na$_2$SO$_4$, filtered, and concentrated to a colorless oil. Trituration with Et$_2$O afforded N'-{5-fluoro-2-[1-phenylmethylideneaminooxy]pyrimidin-4-yl}-N,N-dimethylformamidine (0.054 g, 31%) as a white solid: mp 240-244° C. dec; $^1$H NMR (400 MHz, CDCl$_3$) δ 8.73 (s, 1H), 8.53 (s, 1H), 8.19 (d, J=2.4 Hz, 1H), 7.81-7.69 (m, 2H), 7.49-7.30 (m, 3H), 3.21 (s, 3H), 3.21 (s, 3H); ESIMS m/z 288 ([M+H]$^+$).

Compounds 2 and 3 in Table I were prepared as in Example 1.

Example 2

Preparation of N-{5-fluoro-2-[1-phenylmethylidene-amino-oxy]pyrimidin-4-yl}formamide (4)

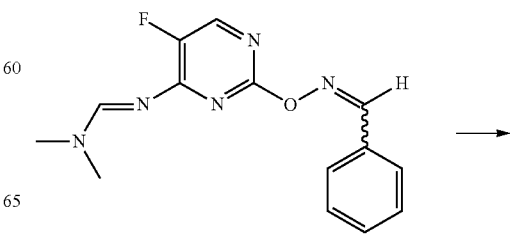

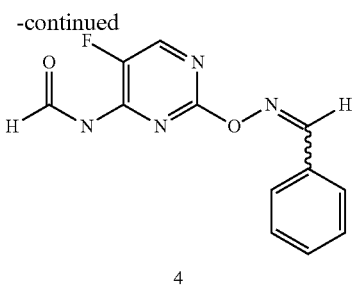

4

To a suspension of N'-{5-fluoro-2-[1-phenylmethylideneaminooxy]pyrimidin-4-yl}-N,N-dimethylformamidine (0.035 g, 0.12 mmol) in dioxane (1.2 mL) was added dilute hydrochloric acid (HCl, 1 N, 0.006 g, 0.16 mmol) and the mixture was stirred at 23° C. for 16 h. The reaction mixture was purified by flash chromatography (4 g SiO$_2$; 0→60% EtOAc/hexanes) to give N-{5-fluoro-2-[1-phenylmethylideneaminooxy]pyrimidin-4-yl}formamide (0.007 g, 22%) as a white solid: mp 210-232° C. dec; $^1$H NMR (400 MHz, DMSO-d$_6$) δ 11.43 (s, 1H), 9.36 (s, 1H), 8.79 (s, 1H), 8.57 (d, J=2.4 Hz, 1H), 7.80 (dd, J=7.7, 1.6 Hz, 2H), 7.52 (m, 3H); ESIMS m/z 261 ([M+H]$^+$), 259 ([M−H]$^−$).

Example 3

Preparation of 2-chlorobenzaldehyde O-(4-amino-5-fluoropyrimidin-2-yl)oxime (5)

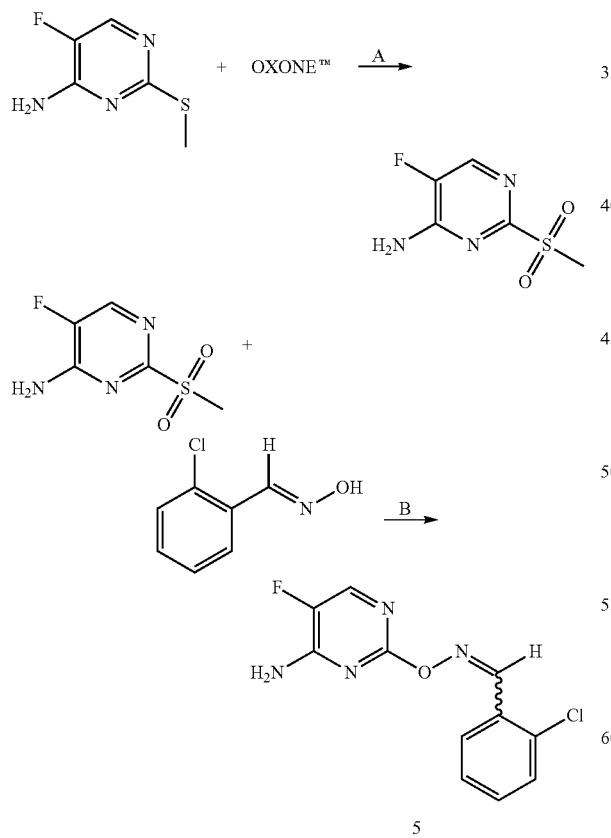

Step A. To a solution of 5-fluoro-2-methylsulfanylpyrimidin-4-ylamine (5.02 g, 31.6 mmol) in methyl alcohol (MeOH; 105 mL) was added dropwise a solution of OXONE™ (Registered trademark of E.I. du Pont de Nemours & Co, Inc.; 42.7 g, 69.4 mmol) in H$_2$O (210 mL) over a 20 minute (min) period at −45° C., and the resulting mixture was slowly warmed to 10° C. over a period of 14 h. The mixture was treated with sodium bisulfite (10 g) and the majority of the MeOH was removed on the rotary evaporator. The aqueous residue was extracted with EtOAc (2×250 mL), and the organic extracts were combined, washed with brine (100 mL), dried over Na$_2$SO$_4$, filtered, and concentrated to give 5-fluoro-2-methanesulfonylpyrimidin-4-ylamine (3.79 g, 63%) as a white solid: mp 157-159° C.; $^1$H NMR (300 MHz, DMSO-d$_6$) δ 8.35 (d, J=3.6 Hz, 1H), 8.11 (s, 2H), 3.27 (s, 3H); CIMS m/z 191 ([M]$^+$).

Step B. To a suspension of 60% NaH (0.063 g, 1.57 mmol) in anhydrous tetrahydrofuran (THF; 5 mL) was added in portions a solution of 2-chlorobenzaldehyde oxime (0.254 g, 1.64 mmol in 1 mL of THF) at room temperature, and the resulting frothy mixture was stirred for 1 h. To the resulting tan mixture was added 5-fluoro-2-methanesulfonylpyrimidin-4-ylamine (0.25 g, 1.31 mmol), at which point the reaction mixture turned orange and most of the solids dissolved. Within minutes of the addition a new solid had precipitated, and the resulting orange mixture was stirred at room temperature for 16 h. The entire reaction mixture was adsorbed to Celite (2.5 g) and the adsorbed material was purified by flash chromatography (24 g SiO$_2$; 0→100% EtOAc/hexanes) to give 2-chlorobenzaldehyde O-(4-amino-5-fluoropyrimidin-2-yl)oxime (0.173 g, 50%) as a white solid: mp 220-230° C. dec; $^1$H NMR (400 MHz, DMSO-d$_6$) δ 8.83 (s, 1H), 8.05 (d, J=3.1 Hz, 1H), 7.92 (dd, J=7.8, 1.5 Hz, 1H), 7.54 (m, 5H); ESIMS m/z 267 ([M+H]$^+$), 265 ([M−H]$^−$).

Compounds 6-12 in Table I were prepared as in Example 3.

Example 4

Preparation of N'-{5-Fluoro-2-[1-(4-methoxyphenyl)-methylideneaminooxy]pyrimidin-4-yl}-N,N-dimethylformamidine (13)

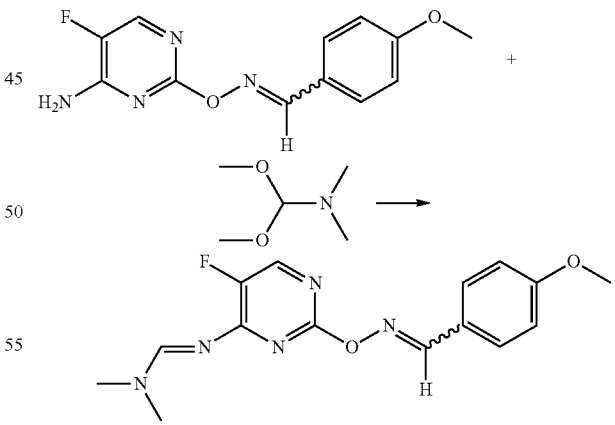

To a magnetically stirred suspension of 4-methoxybenzaldehyde O-(4-amino-5-fluoropyrimidin-2-yl)oxime (0.075 g, 0.29 mmol) in anhydrous DMF (0.2 mL) was added DMF-DMA (0.068 g, 0.57 mmol) and the resulting mixture was stirred at room temperature for 3 h. The reaction mixture was diluted with Et$_2$O (10 mL) and then was cooled to 0° C. The resulting solid was collected by vacuum filtration, and the cake was washed with cold Et$_2$O followed by hexanes. The precipitate that formed in the filtrate was collected by vacuum filtration and the combined solids were dried under vacuum to give N'-{5-fluoro-2-[1-(4-methoxyphenyl)-methylideneaminooxy]pyrimidin-4-yl}-N,N-dimethylformamidine (0.069 g, 76%) as a white solid: mp 243-245° C. dec; $^1$H NMR (300 MHz, DMSO-$d_6$) δ 8.68 (s, 1H), 8.60 (s, 1H), 8.26 (d, J=2.7 Hz, 1H), 7.73 (d, J=8.6 Hz, 2H), 7.05 (d, J=8.6 Hz, 2H), 3.82 (s, 3H), 3.21 (s, 3H), 3.10 (s, 3H); ESIMS m/z 318 ([M+H]$^+$).

Compounds 14 and 15 were prepared as in Example 4.

Example 5

Preparation of 2-methylpropionaldehyde O-[5-fluoro-4-(2-fluorobenzylamino)pyrimidin-2-yl]oxime (16)

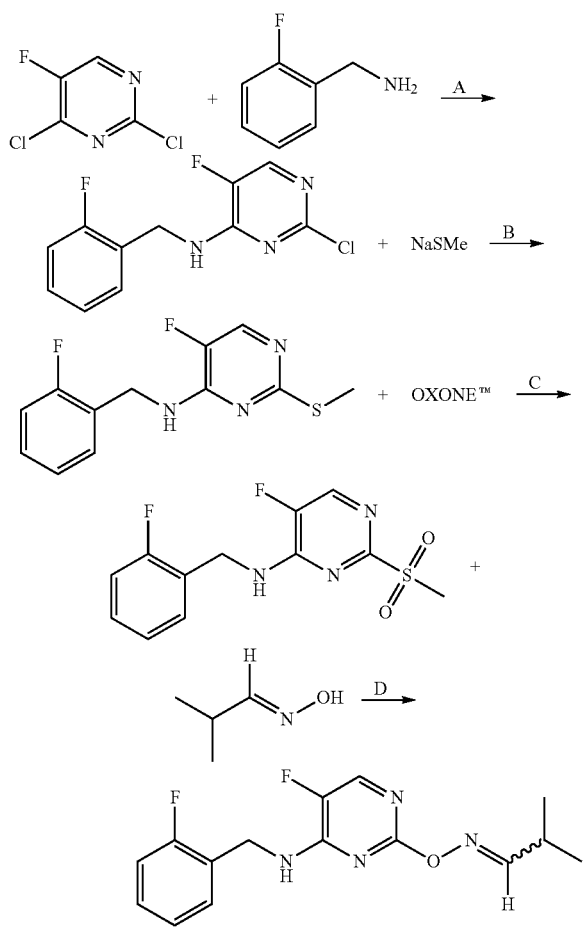

Step A. To a magnetically stirred solution of 2,4-dichloro-5-fluoropyrimidine (0.105 g, 0.63 mmol) in anhydrous THF (5 mL) were added 2-fluorobenzylamine (0.085 g, 0.68 mmol) and triethylamine (0.127 g, 1.26 mmol), and the mixture was warmed to reflux and stirred for 5 h. The reaction mixture was cooled to room temperature and partitioned between CH$_2$Cl$_2$ (15 mL) and 1 N HCl (10 mL). The phases were separated and the aqueous phase was extracted with additional CH$_2$Cl$_2$ (15 mL). The combined organic extracts were washed with brine, dried over Na$_2$SO$_4$, and filtered. The solvent was removed under reduced pressure to yield (2-chloro-5-fluoropyrimidin-4-yl)-(2-fluorobenzyl)amine (0.157 g, 97%) as a yellow solid: mp 117-118° C.; $^1$H NMR (300 MHz, CDCl$_3$) δ 7.95 (s, 1H), 7.45 (t, 1H), 7.35 (m, 1H), 7.15 (m, 2H), 5.60 (br s, 1H), 4.80 (d, 2H); ESIMS m/z 256 ([M+H]$^+$). Alternatively, 2-chloro-5-fluoropyrimidin-4-yl)-(2-fluorobenzyl)amine was prepared using methods known in the literature, such as Boebel, T. et al. U.S. Patent Application Publication 2010/0022538.

Step B. To a solution of (2-chloro-5-fluoropyrimidin-4-yl)-(2-fluorobenzyl)amine (2.0 g, 7.82 mmol) in EtOH (78 mL) was added NaSCH$_3$ (1.10 g, 15.6 mmol), and the resulting turbid mixture was warmed to reflux and stirred for 10 h. The reaction mixture was cooled to room temperature, the solvent was evaporated, and the residue was partitioned between EtOAc (100 mL) and H$_2$O (100 mL). The phases were separated, and the aqueous phase was extracted with additional EtOAc (100 mL). The organic extracts were combined, dried over Na$_2$SO$_4$, filtered, and concentrated to an off-white solid. The solid was purified by flash chromatography (80 g SiO$_2$; 0→50% EtOAc/hexanes) to give (2-fluorobenzyl)-(5-fluoro-2-methylsulfanylpyrimidin-4-yl)amine (2.07 g, 99%) as a white solid: mp 144-146° C.; $^1$H NMR (400 MHz, CDCl$_3$) δ 7.89 (d, J=3.2 Hz, 1H), 7.39 (td, J=7.5, 1.5 Hz, 1H), 7.30 (ddd, J=7.9, 4.7, 1.9 Hz, 1H), 7.16-7.03 (m, 2H), 5.39 (s, 1H), 4.76 (d, J=6.0 Hz, 2H), 2.50 (s, 3H); CIMS m/z 267 ([M]$^+$).

Step C. To a solution of (2-fluorobenzyl)-(5-fluoro-2-methylsulfanylpyrimidin-4-yl)amine (2.10 g, 7.86 mmol) in MeOH (26 mL) was added a solution of OXONE™ (10.14 g, 16.5 mmol) in H$_2$O (52 mL) dropwise over a 20 min period at −45° C., and the resulting mixture was slowly warmed to 10° C. over a period of 14 h. The mixture was treated with sodium bisulfite (~3 g) and the majority of the MeOH was removed on the rotary evaporator. The aqueous residue was extracted with EtOAc (3×150 mL), and the organic extracts were combined, washed with brine (100 mL), dried over Na$_2$SO$_4$, filtered, and concentrated to give a peach solid. The solid was purified by flash chromatography (40 g SiO$_2$; 0→100% EtOAc/hexanes) to give 2-fluorobenzyl-(5-fluoro-2-methanesulfonylpyrimidin-4-yl)amine (1.99 g, 85%) as a white solid: mp 105-107° C.; $^1$H NMR (400 MHz, CDCl$_3$) δ 8.10 (d, J=2.9 Hz, 1H), 7.46 (td, J=7.6, 1.7 Hz, 1H), 7.31 (m, 1H), 7.14 (td, J=7.5, 1.1 Hz, 1H), 7.08 (m, 1H), 5.89 (s, 1H), 4.82 (d, J=6.0 Hz, 2H), 3.25 (s, 3H); CIMS m/z 299 ([M]$^+$).

Step D. To a solution of 2-methylpropionaldehyde oxime (0.047 g, 0.54 mmol) in anhydrous THF (3 mL) was added a solution of potassium tert-butoxide (KO$^t$Bu, 1 M in THF; 0.50 mL, 0.50 mmol) at room temperature, and the resulting pale-yellow mixture was stirred for 15 min. To the resulting solution was added 2-fluorobenzyl-(5-fluoro-2-methanesulfonylpyrimidin-4-yl)amine (0.125 g, 0.42 mmol), and the resulting tan mixture was stirred at room temperature for 16 h. The entire reaction mixture was adsorbed to Celite (2.5 g) and the adsorbed material was purified by flash chromatography (40 g SiO$_2$; 0→100% EtOAc/hexanes) to give 2-methylpropionaldehyde O-[5-fluoro-4-(2-fluorobenzylamino)-pyrimidin-2-yl]oxime (0.71 g, 56%) as a colorless oil: IR (thin film) 3261, 3179, 3049, 2973, 2936, 2872, 1676, 1622, 1568, 1531, 1491, 1457, 1409, 1372 cm$^{-1}$; $^1$H NMR (400 MHz, CDCl$_3$) δ 7.91 (d, J=2.5 Hz, 1H), 7.71 (d, J=7.5 Hz, 1H), 7.43 (t, J=6.9 Hz, 1H), 7.29 (m, J=7.6 Hz, 1H), 7.09 (m, 2H), 5.42 (s, 1H), 4.76 (d, J=5.8 Hz, 2H), 2.79 (dq, J=13.9, 6.9 Hz, 1H), 1.18 (d, J=6.8 Hz, 6H); ESIMS m/z 307 ([M+H]$^+$), 305 ([M−H]$^−$).

Compounds 17-55 were prepared as in Example 5.

TABLE I

Compounds and Their Structures

| Compound | Structure |
|---|---|
| 2 | 5-fluoro-4-(dimethylaminomethyleneamino)-2-[(4-chlorobenzylidene)aminooxy]pyrimidine |
| 3 | 5-fluoro-4-(dimethylaminomethyleneamino)-2-[(2-chlorobenzylidene)aminooxy]pyrimidine |
| 6 | 5-fluoro-4-amino-2-[(benzylidene)aminooxy]pyrimidine |
| 7 | 5-fluoro-4-amino-2-[(isobutylidene)aminooxy]pyrimidine |
| 8 | 5-fluoro-4-amino-2-[(4-chlorobenzylidene)aminooxy]pyrimidine |
| 9 | 5-fluoro-4-amino-2-[(2-methoxybenzylidene)aminooxy]pyrimidine |
| 10 | 5-fluoro-4-amino-2-[(ethylidene)aminooxy]pyrimidine |
| 11 | 5-fluoro-4-amino-2-[(4-methylbenzylidene)aminooxy]pyrimidine |
| 12 | 5-fluoro-4-amino-2-[(4-methoxybenzylidene)aminooxy]pyrimidine |
| 14 | 5-fluoro-4-(dimethylaminomethyleneamino)-2-[(2-methoxybenzylidene)aminooxy]pyrimidine |

TABLE I-continued
Compounds and Their Structures
| Compound | Structure |
|---|---|
| 15 | 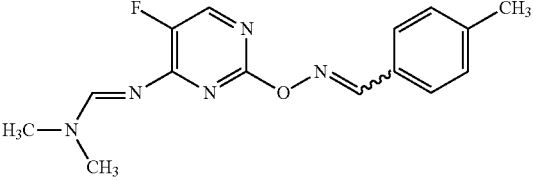 |
| 17 | 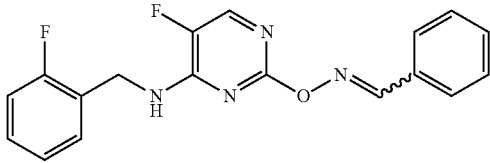 [SMILES: Fc1ccccc1CNc1nc(ON=Cc2ccccc2)ncc1F] |
| 18 | 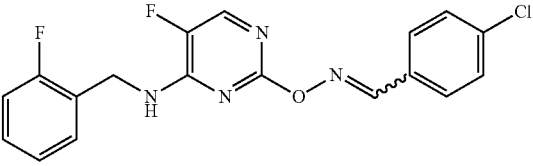 [SMILES: Fc1ccccc1CNc1nc(ON=Cc2ccc(Cl)cc2)ncc1F] |
| 19 | 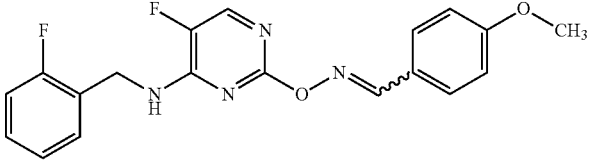 [SMILES: COc1ccc(C=NOc2ncc(F)c(NCc3ccccc3F)n2)cc1] |
| 20 | 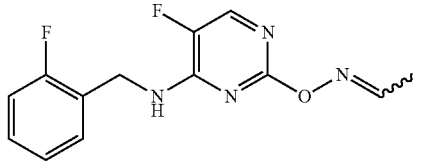 |
| 21 | 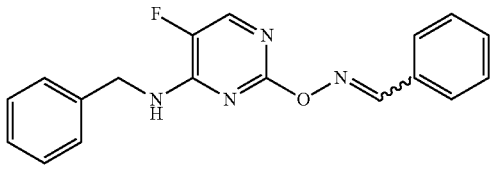 [SMILES: Fc1cnc(ON=Cc2ccccc2)nc1NCc1ccccc1] |
| 22 | 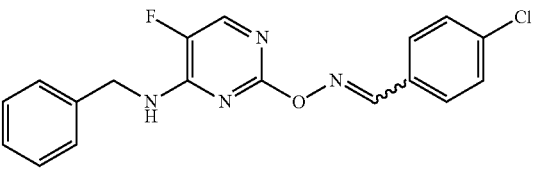 [SMILES: Fc1cnc(ON=Cc2ccc(Cl)cc2)nc1NCc1ccccc1] |
| 23 | 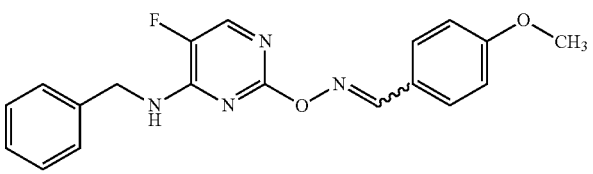 [SMILES: COc1ccc(C=NOc2ncc(F)c(NCc3ccccc3)n2)cc1] |

TABLE I-continued
Compounds and Their Structures
| Compound | Structure |
|---|---|
| 24 | 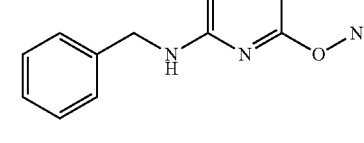 |
| 25 | 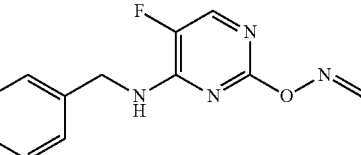 |
| 26 | 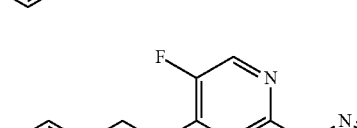 |
| 27 | 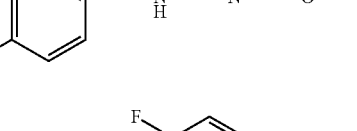 |
| 28 | 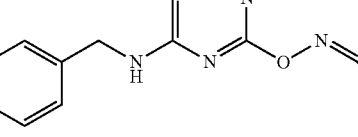 |
| 29 | 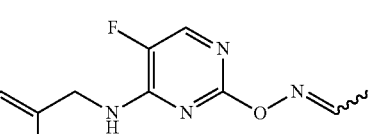 |
| 30 | 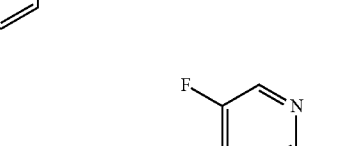 |
| 31 | 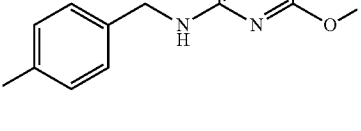 |

TABLE I-continued

Compounds and Their Structures

| Compound | Structure |
|---|---|
| 32 | 4-methoxybenzyl-amino group on 5-fluoropyrimidine with O-N=CH-(4-chlorophenyl) oxime |
| 33 | 4-methoxybenzyl-amino group on 5-fluoropyrimidine with O-N=CH-(4-methoxyphenyl) oxime |
| 34 | 4-methoxybenzyl-amino group on 5-fluoropyrimidine with O-N=CH-CH₃ oxime |
| 35 | 4-methoxybenzyl-amino group on 5-fluoropyrimidine with O-N=CH-CH(CH₃)₂ oxime |
| 36 | N-benzyl-N-methyl-amino group on 5-fluoropyrimidine with O-N=CH-phenyl oxime |
| 37 | N-benzyl-N-methyl-amino group on 5-fluoropyrimidine with O-N=CH-(4-chlorophenyl) oxime |
| 38 | N-benzyl-N-methyl-amino group on 5-fluoropyrimidine with O-N=CH-(4-methoxyphenyl) oxime |
| 39 | N-benzyl-N-methyl-amino group on 5-fluoropyrimidine with O-N=CH-CH₃ oxime |

TABLE I-continued

Compounds and Their Structures

| Compound | Structure |
|---|---|
| 40 | 4-F-5-fluoropyrimidine with N(CH3)(benzyl) at 4-position and O-N=CH-CH(CH3)2 at 2-position |
| 41 | 5-fluoropyrimidine with N(CH3)(4-chlorobenzyl) at 4-position and O-N=CH-phenyl at 2-position |
| 42 | 5-fluoropyrimidine with N(CH3)(4-chlorobenzyl) at 4-position and O-N=CH-(4-chlorophenyl) at 2-position |
| 43 | 5-fluoropyrimidine with N(CH3)(4-chlorobenzyl) at 4-position and O-N=CH-(4-methoxyphenyl) at 2-position |
| 44 | 5-fluoropyrimidine with N(CH3)(4-chlorobenzyl) at 4-position and O-N=CH-CH3 at 2-position |
| 45 | 5-fluoropyrimidine with N(CH3)(4-chlorobenzyl) at 4-position and O-N=CH-CH(CH3)2 at 2-position |
| 46 | 5-fluoropyrimidine with N(CH3)(4-methoxybenzyl) at 4-position and O-N=CH-phenyl at 2-position |
| 47 | 5-fluoropyrimidine with N(CH3)(4-methoxybenzyl) at 4-position and O-N=CH-(4-chlorophenyl) at 2-position |

TABLE I-continued

Compounds and Their Structures

| Compound | Structure |
|---|---|
| 48 | 4-methoxybenzyl(methyl)amino-5-fluoropyrimidin-2-yl O-(4-methoxybenzylidene)oxime |
| 49 | 4-methoxybenzyl(methyl)amino-5-fluoropyrimidin-2-yl O-ethylideneoxime |
| 50 | 4-methoxybenzyl(methyl)amino-5-fluoropyrimidin-2-yl O-(2-methylpropylidene)oxime |
| 51 | 4-dimethylamino-5-fluoropyrimidin-2-yl O-benzylideneoxime |
| 52 | 4-dimethylamino-5-fluoropyrimidin-2-yl O-(4-chlorobenzylidene)oxime |
| 53 | 4-dimethylamino-5-fluoropyrimidin-2-yl O-(4-methoxybenzylidene)oxime |
| 54 | 4-dimethylamino-5-fluoropyrimidin-2-yl O-ethylideneoxime |
| 55 | 4-dimethylamino-5-fluoropyrimidin-2-yl O-(2-methylpropylidene)oxime |

TABLE II

Characterization Data for the Compounds in Table I

| Compound | ESIMS m/z | mp (° C.) | Appearance | IR (thin film, cm$^{-1}$) | $^1$H NMR (field strength, solvent) |
|---|---|---|---|---|---|
| 2 | 324 [M + 3] | 230-242 dec | white solid | | (400 MHz, CDCl$_3$) δ 8.71 (s, 1H), 8.49 (s, 1H), 8.18 (s, 1H), 7.72 (d, J = 8.5 Hz, 2H), 7.41 (d, J = 8.5 Hz, 2H), 3.21 (s, 3H), 3.21 (s, 3H) |
| 3 | 324 [M + 3] | 186-210 dec | white solid | | (400 MHz, CDCl$_3$) δ 8.99 (s, 1H), 8.73 (s, 1H), 8.16 (m, 2H), 7.37 (m, 3H), 3.22 (s, 3H), 3.21 (s, 3H) |
| 6 | 233 | 151-153 | white solid | | (300 MHz, CDCl$_3$) δ 8.50 (s, 1H), 8.04 (d, J = 2.5 Hz, 1H), 7.76 (m, 2H), 7.44 (m, 3H), 5.43 (s, 2H) |
| 7 | 199 ([M + H]$^+$), 197 ([M − H]$^-$) | 105-107 | white solid | | (400 MHz, DMSO-d$_6$) δ 7.96 (d, J = 3.2 Hz, 1H), 7.75 (d, J = 6.5 Hz, 1H), 7.41 (s, 2H), 2.59 (dq, J = 13.6, 6.8 Hz, 1H), 1.10 (d, J = 6.8 Hz, 6H) |
| 8 | 267 ([M + H]$^+$) | 200-220 dec | white solid | | (300 MHz, CDCl$_3$) δ 8.69 (s, 1H), 8.03 (d, J = 3.2 Hz, 1H), 7.77 (d, J = 8.6 Hz, 2H), 7.58 (d, J = 8.5 Hz, 2H), 7.52 (s, 2H) |
| 9 | 263 ([M + H]$^+$), 261 ([M − H]$^-$) | 240-250 dec | white solid | | (300 MHz, CDCl$_3$) δ 8.90 (s, 1H), 8.02 (d, J = 2.6 Hz, 1H), 7.97 (dd, J = 7.7, 1.7 Hz, 1H), 7.43 (m, 1H), 6.99 (t, J = 7.4 Hz, 1H), 6.93 (d, J = 8.4 Hz, 1H), 5.51 (s, 2H), 3.88 (s, 3H) |
| 10 | 171 ([M + H]$^+$) | 102-105 | white solid | | (300 MHz, CDCl$_3$) δ 7.99 (d, J = 2.6 Hz, 1H), 7.87 (q, J = 5.9 Hz, 1H), 5.57 (s, 2H), 2.08 (d, J = 5.9 Hz, 3H) |
| 11 | 247 ([M + H]$^+$), 245 ([M − H]$^-$) | 201-220 dec | white solid | | (300 MHz, DMSO-d$_6$) δ 8.61 (s, 1H), 8.02 (d, J = 2.7 Hz, 1H), 7.64 (d, J = 7.8 Hz, 2H), 7.48 (s, 2H), 7.30 (d, J = 7.7 Hz, 2H), 2.36 (s, 3H) |
| 12 | 263 ([M + H]$^+$), 261 ([M − H]$^-$) | 250-270 dec | white solid | | (300 MHz, DMSO-d$_6$) δ 8.57 (s, 1H), 8.01 (d, J = 3.2 Hz, 1H), 7.70 (d, J = 8.8 Hz, 2H), 7.47 (s, 2H), 7.05 (d, J = 8.8 Hz, 2H), 3.82 (s, 3H) |
| 14 | 318 ([M + H]$^+$) | 220-230 dec | white solid | | (300 MHz, DMSO-d$_6$) δ 8.74 (s, 1H), 8.67 (s, 1H), 8.27 (d, J = 2.8 Hz, 1H), 7.81 (dd, J = 7.7, 1.6 Hz, 1H), 7.52 (m, 1H), 7.16 (d, J = 8.4 Hz, 1H), 7.05 (t, J = 7.5 Hz, 1H), 3.88 (s, 3H), 3.21 (s, 3H), 3.10 (s, 3H) |
| 15 | 302 ([M + H]$^+$) | 247-253 dec | white solid | | (300 MHz, DMSO-d$_6$) δ 8.68 (s, 1H), 8.63 (s, 1H), 8.26 (s, 1H), 7.67 (d, J = 7.6 Hz, 2H), 7.31 (d, J = 7.5 Hz, 2H), 3.21 (s, 3H), 3.10 (s, 3H), 2.36 (s, 3H) |

TABLE II-continued

Characterization Data for the Compounds in Table I

| Compound | ESIMS m/z | mp (° C.) | Appearance | IR (thin film, cm$^{-1}$) | $^1$H NMR (field strength, solvent) |
|---|---|---|---|---|---|
| 17 | 341 ([M + H]$^+$) | | colorless viscous oil | 3437, 3267, 3178, 2937, 1625, 1527, 1490, 1457, 1391, 1373, 1265 | (400 MHz, CDCl$_3$) δ 8.52 (s, 1H), 7.95 (m, 1H), 7.77 (m, 2H), 7.45 (m, 4H), 7.29 (d, J = 7.1 Hz, 1H), 7.09 (m, 2H), 5.52 (s, 1H), 4.79 (d, J = 5.9 Hz, 2H) |
| 18 | 375 ([M + H]$^+$), 373 ([M − H]$^-$) | 98-103 | white solid | | (400 MHz, CDCl$_3$) δ 8.48 (s, 1H), 7.95 (d, J = 2.7 Hz, 1H), 7.71 (m, 2H), 7.47 (td, J = 7.5, 1.7 Hz, 1H), 7.40 (m, 2H), 7.29 (m, 1H), 7.10 (m, 2H), 5.50 (s, 1H), 4.79 (d, J = 5.9 Hz, 2H) |
| 19 | 371 ([M + H]$^+$), 369 ([M − H]$^-$) | | colorless viscous oil | 3440, 3267, 3177, 3045, 2938, 1623, 1526, 1514, 1374, 1257, 1171 | (400 MHz, CDCl$_3$) δ 8.46 (s, 1H), 7.94 (d, J = 2.7 Hz, 1H), 7.72 (m, 2H), 7.48 (td, J = 7.5, 1.6 Hz, 1H), 7.28 (dd, J = 7.9, 2.1 Hz, 1H), 7.10 (m, 2H), 6.93 (m, 2H), 5.46 (s, 1H), 4.79 (d, J = 5.9 Hz, 2H), 3.84 (s, 3H) |
| 20 | 279 ([M + H]$^+$) | 99-100 | white solid | | (400 MHz, CDCl$_3$) δ 7.91 (m, 2H), 7.42 (dd, J = 8.3, 6.7 Hz, 1H), 7.30 (m, 1H), 7.10 (m, 2H), 5.38 (s, 1H), 4.77 (d, J = 5.9 Hz, 2H), 2.08 (d, J = 5.9 Hz, 3H) |
| 21 | 323 ([M + H]$^+$) | 111-113 | white solid | | (300 MHz, CDCl$_3$) δ 8.53 (s, 1H), 7.97 (d, J = 2.7 Hz, 1H), 7.77 (dd, J = 7.6, 1.8 Hz, 2H), 7.38 (m, 8H), 5.40 (s, 1H), 4.74 (d, J = 5.6 Hz, 2H) |
| 22 | 357 ([M + H]$^+$) | 111-114 | white solid | | (301 MHz, CDCl$_3$) δ 8.45 (s, 1H), 7.93 (d, J = 2.6 Hz, 1H), 7.68 (d, J = 8.5 Hz, 2H), 7.34 (m, 7H), 5.46 (s, 1H), 4.71 (d, J = 5.6 Hz, 2H) |
| 23 | 353 ([M + H]$^+$) | 180-194 | white solid | | (300 MHz, CDCl$_3$) δ 8.44 (s, 1H), 7.92 (d, J = 2.7 Hz, 1H), 7.70 (m, 2H), 7.33 (m, 5H), 6.92 (d, J = 8.8 Hz, 2H), 5.62 (s, 1H), 4.71 (d, J = 5.6 Hz, 2H), 3.82 (s, 3H) |
| 24 | 261 ([M + H]$^+$) | | colorless oil | | (300 MHz, CDCl$_3$) δ 7.90 (m, 2H), 7.33 (m, 5H), 5.41 (s, 1H), 4.70 (d, J = 5.6 Hz, 2H), 2.07 (d, J = 5.9 Hz, 3H) |
| 25 | 289 ([M + H]$^+$) | | colorless oil | 3390, 3049, 2926, 1639, 1554, 1462, 1449, 1410 | (300 MHz, CDCl$_3$) δ 7.92 (d, J = 2.7 Hz, 1H), 7.70 (d, J = 7.6 Hz, 1H), 7.35 (m, 5H), 5.38 (s, 1H), 4.70 (d, J = 5.6 Hz, 2H), 2.79 (dq, J = 14.0, 6.9 Hz, 1H), 1.18 (d, J = 6.8 Hz, 6H) |
| 26 | 357 ([M + H]$^+$) | 127-128 | white solid | | (300 MHz, CDCl$_3$) δ 8.52 (s, 1H), 7.98 (d, J = 2.7 Hz, 1H), 7.76 (dd, J = 7.6, 1.8 Hz, 2H), 7.44 (m, 3H), 7.33 (s, 4H), 5.45 (s, |

TABLE II-continued

Characterization Data for the Compounds in Table I

| Compound | ESIMS m/z | mp (° C.) | Appearance | IR (thin film, cm$^{-1}$) | $^1$H NMR (field strength, solvent) |
|---|---|---|---|---|---|
| 27 | 391 ([M + H]$^+$) | 119-121 | white solid | | 1H), 4.71 (d, J = 5.8 Hz, 2H) (300 MHz, CDCl$_3$) δ 8.46 (s, 1H), 7.96 (d, J = 2.6 Hz, 1H), 7.69 (d, J = 8.5 Hz, 2H), 7.39 (d, J = 8.6 Hz, 2H), 7.31 (s, 4H), 5.40 (s, 1H), 4.69 (d, J = 5.8 Hz, 2H) |
| 28 | 387 ([M + H]$^+$) | 141-142 | white solid | | (300 MHz, CDCl$_3$) δ 8.44 (s, 1H), 7.95 (d, J = 2.7 Hz, 1H), 7.69 (d, J = 8.8 Hz, 2H), 7.31 (s, 4H), 6.93 (d, J = 8.8 Hz, 2H), 5.57 (s, 1H), 4.69 (d, J = 5.8 Hz, 2H), 3.84 (s, 3H) |
| 29 | 295 ([M + H]$^+$) | 116-117 | white solid | | (300 MHz, CDCl$_3$) δ 7.91 (m, 2H), 7.31 (dd, J = 15.4, 10.3 Hz, 4H), 5.37 (s, 1H), 4.68 (d, J = 5.7 Hz, 2H), 2.08 (d, J = 6.0 Hz, 3H) |
| 30 | 323 ([M + H]$^+$) | 200-205 | white solid | | (300 MHz, CDCl$_3$) δ 7.94 (d, J = 2.6 Hz, 1H), 7.70 (d, J = 7.6 Hz, 1H), 7.31 (m, 4H), 5.35 (s, 1H), 4.68 (d, J = 5.8 Hz, 2H), 2.80 (m, 1H), 1.18 (d, J = 6.8 Hz, 6H) |
| 31 | 353 ([M + H]$^+$) | | white oil | 3361, 1641, 1570, 1512, 1446, 1423, 1366, 1239, 1022 | (300 MHz, CDCl$_3$) δ 8.53 (s, 1H), 7.97 (d, J = 2.8 Hz, 1H), 7.78 (dd, J = 7.6, 1.9 Hz, 2H), 7.44 (dd, J = 6.9, 5.3 Hz, 3H), 7.32 (d, J = 8.7 Hz, 2H), 6.89 (d, J = 8.7 Hz, 2H), 5.37 (s, 1H), 4.66 (d, J = 5.5 Hz, 2H), 3.81 (s, 3H) |
| 32 | 387 ([M + H]$^+$) | | colorless oil | | (300 MHz, CDCl$_3$) δ 8.49 (s, 1H), 7.96 (d, J = 2.7 Hz, 1H), 7.72 (d, J = 8.5 Hz, 2H), 7.40 (d, J = 8.5 Hz, 2H), 7.31 (d, J = 8.7 Hz, 2H), 6.90 (d, J = 8.7 Hz, 2H), 5.36 (s, 1H), 4.65 (d, J = 5.5 Hz, 2H), 3.81 (s, 3H) |
| 33 | 383 ([M + H]$^+$) | | colorless oil | 2908, 1629, 1605, 1510, 1417, 1347, 1301, 1246, 1169, 1032, 958 | (300 MHz, CDCl$_3$) δ 8.46 (s, 1H), 7.94 (d, J = 2.7 Hz, 1H), 7.71 (d, J = 8.8 Hz, 2H), 7.31 (d, J = 8.7 Hz, 2H), 6.91 (dd, J = 12.7, 8.8 Hz, 4H), 5.40 (s, 1H), 4.65 (d, J = 5.5 Hz, 2H), 3.84 (s, 3H), 3.80 (s, 3H) |
| 34 | 291 ([M + H]$^+$) | 79-82 | white solid | | (300 MHz, CDCl$_3$) δ 7.90 (m, 2H), 7.28 (d, J = 8.5 Hz, 2H), 6.89 (d, J = 8.6 Hz, 2H), 5.33 (s, 1H), 4.62 (d, J = 5.4 Hz, 2H), 3.81 (s, 3H), 2.08 (d, J = 5.9 Hz, 3H) |
| 35 | 319 ([M + H]$^+$) | | colorless oil | 3360, 3156, 3081, 1658, 1642, 1568, 1511, 1446, 1423, 1212, | (300 MHz, CDCl$_3$) δ 7.92 (d, J = 2.7 Hz, 1H), 7.71 (d, J = 7.6 Hz, 1H), 7.29 (d, J = 8.4 Hz, 2H), 6.89 (d, |

TABLE II-continued

Characterization Data for the Compounds in Table I

| Compound | ESIMS m/z | mp (° C.) | Appearance | IR (thin film, cm$^{-1}$) | $^1$H NMR (field strength, solvent) |
|---|---|---|---|---|---|
| | | | | 1021, 551 | J = 8.3 Hz, 2H), 5.35 (s, 1H), 4.62 (d, J = 5.5 Hz, 2H), 3.81 (s, 3H), 2.80 (dq, J = 13.9, 6.9 Hz, 1H), 1.18 (d, J = 6.8 Hz, 6H) |
| 36 | 337 ([M + H]$^+$) | | colorless oil | 3029, 1660, 1602, 1571, 1511, 1449, 1400, 1355, 1321, 1301, 1248, 1222, 1023 | (300 MHz, CDCl$_3$) δ 8.50 (s, 1H), 7.99 (d, J = 6.1 Hz, 1H), 7.75 (dd, J = 7.6, 1.9 Hz, 2H), 7.36 (m, 8H), 4.86 (s, 2H), 3.21 (d, J = 2.9 Hz, 3H) |
| 37 | 371 ([M + H]$^+$) | 78-81 | white solid | | (300 MHz, CDCl$_3$) δ 8.44 (s, 1H), 7.98 (d, J = 6.1 Hz, 1H), 7.67 (d, J = 8.5 Hz, 2H), 7.31 (m, 7H), 4.85 (s, 2H), 3.21 (d, J = 2.9 Hz, 3H) |
| 38 | 367 ([M + H]$^+$) | 100-103 | white solid | | (300 MHz, CDCl$_3$) δ 8.44 (s, 1H), 8.00 (d, J = 6.1 Hz, 1H), 7.70 (d, J = 8.8 Hz, 2H), 7.30 (m, 5H), 6.92 (d, J = 8.8 Hz, 2H), 4.85 (s, 2H), 3.82 (s, 3H), 3.20 (d, J = 2.8 Hz, 3H) |
| 39 | 275 ([M + H]$^+$) | | colorless oil | 3046, 2919, 2848, 2784, 1631, 1527, 1511, 1451, 1431, 1395, 1353 | (300 MHz, CDCl$_3$) δ 7.97 (d, J = 6.1 Hz, 1H), 7.88 (q, J = 5.9 Hz, 1H), 7.32 (m, 5H), 4.84 (s, 2H), 3.17 (d, J = 2.8 Hz, 3H), 2.06 (d, J = 5.9 Hz, 3H) |
| 40 | 303 ([M + H]$^+$) | 176-179 | white solid | | (300 MHz, CDCl$_3$) δ 7.96 (d, J = 6.1 Hz, 1H), 7.69 (d, J = 7.5 Hz, 1H), 7.31 (m, 5H), 4.83 (s, 2H), 3.18 (d, J = 2.8 Hz, 3H), 2.78 (m, 1H), 1.17 (d, J = 6.8 Hz, 6H) |
| 41 | 371 ([M + H]$^+$) | | colorless oil | 3193, 3077, 2924, 1636, 1529, 1492, 1451, 1403, 1337, 1221, 799 | (300 MHz, CDCl$_3$) δ 8.51 (s, 1H), 8.03 (d, J = 6.0 Hz, 1H), 7.76 (dd, J = 7.7, 1.8 Hz, 2H), 7.42 (m, 3H), 7.28 (m, 4H), 4.82 (s, 2H), 3.21 (d, J = 3.0 Hz, 3H) |
| 42 | 407 ([M + 3H]$^+$) | 115-116 | white solid | | (300 MHz, CDCl$_3$) δ 8.46 (s, 1H), 8.00 (d, J = 6.0 Hz, 1H), 7.68 (d, J = 8.6 Hz, 2H), 7.39 (d, J = 8.6 Hz, 2H), 7.31 (m, 2H), 7.24 (d, J = 8.5 Hz, 2H), 4.81 (s, 2H), 3.21 (d, J = 3.1 Hz, 3H) |
| 43 | 401 ([M + H]$^+$) | | colorless oil | 1659, 1604, 1571, 1531, 1510, 1492, 1402, 1350, 1303, 1255, 1223, 1171 | (300 MHz, CDCl$_3$) δ 8.44 (s, 1H), 8.00 (d, J = 6.0 Hz, 1H), 7.69 (d, J = 8.7 Hz, 2H), 7.31 (d, J = 8.6 Hz, 2H), 7.24 (d, J = 8.5 Hz, 2H), 6.92 (d, J = 8.8 Hz, 2H), 4.81 (s, 2H), 3.83 (s, 3H), 3.20 (d, J = 3.0 Hz, 3H) |
| 44 | 309 ([M + H]$^+$) | 214-220 dec | white solid | | (300 MHz, CDCl$_3$) δ 7.97 (d, J = 6.0 Hz, 1H), 7.88 (q, J = 5.9 Hz, 1H), 7.31 (d, J = 8.4 Hz, 2H), 7.20 (d, |

TABLE II-continued

Characterization Data for the Compounds in Table I

| Compound | ESIMS m/z | mp (° C.) | Appearance | IR (thin film, cm⁻¹) | ¹H NMR (field strength, solvent) |
|---|---|---|---|---|---|
| | | | | | J = 8.4 Hz, 2H), 4.79 (s, 2H), 3.17 (d, J = 2.9 Hz, 3H), 2.07 (d, J = 5.9 Hz, 3H) |
| 45 | 337 ([M + H]⁺) | 224-228 dec | white solid | | (300 MHz, CDCl₃) δ 7.97 (d, J = 6.0 Hz, 1H), 7.69 (d, J = 7.4 Hz, 1H), 7.31 (d, J = 8.5 Hz, 2H), 7.21 (d, J = 8.4 Hz, 2H), 4.79 (s, 2H), 3.17 (d, J = 3.0 Hz, 3H), 2.78 (dq, J = 14.1, 6.9 Hz, 1H), 1.17 (d, J = 6.8 Hz, 6H) |
| 46 | 367 ([M + H]⁺) | | colorless oil | | (300 MHz, CDCl₃) δ 8.51 (s, 1H), 8.04 (d, J = 6.2 Hz, 1H), 7.78 (dd, J = 7.6, 1.9 Hz, 2H), 7.42 (m, 3H), 7.25 (d, J = 8.1 Hz, 2H), 6.87 (d, J = 8.7 Hz, 2H), 4.79 (s, 2H), 3.80 (s, 3H), 3.19 (d, J = 2.9 Hz, 3H) |
| 47 | 401 ([M + H]⁺) | 79-83 | white solid | | (300 MHz, CDCl₃) δ 8.46 (s, 1H), 8.02 (d, J = 6.1 Hz, 1H), 7.70 (d, J = 8.4 Hz, 2H), 7.39 (d, J = 8.5 Hz, 2H), 7.24 (d, J = 8.7 Hz, 2H), 6.87 (d, J = 8.7 Hz, 2H), 4.78 (s, 2H), 3.79 (s, 3H), 3.18 (d, J = 2.9 Hz, 3H) |
| 48 | 397 ([M + H]⁺) | 46-50 | white solid | | (300 MHz, CDCl₃) δ 8.45 (s, 1H), 8.00 (d, J = 6.2 Hz, 1H), 7.71 (d, J = 8.8 Hz, 2H), 7.24 (d, J = 8.6 Hz, 2H), 6.92 (d, J = 8.8 Hz, 2H), 6.87 (d, J = 8.7 Hz, 2H), 4.78 (s, 2H), 3.83 (s, 3H), 3.79 (s, 3H), 3.18 (d, J = 2.9 Hz, 3H) |
| 49 | 305 ([M + H]⁺) | | colorless oil | 3234, 3085, 3022, 2960, 1659, 1534, 1512, 1455, 1349, 1248, 1207 | (300 MHz, CDCl₃) δ 7.95 (d, J = 6.1 Hz, 1H), 7.88 (q, J = 6.0 Hz, 1H), 7.20 (d, J = 8.6 Hz, 2H), 6.87 (d, J = 8.6 Hz, 2H), 4.76 (s, 2H), 3.80 (s, 3H), 3.14 (d, J = 2.8 Hz, 3H), 2.06 (d, J = 5.9 Hz, 3H) |
| 50 | 333 ([M + H]⁺) | 110-112 | white solid | | (300 MHz, CDCl₃) δ 7.95 (d, J = 6.1 Hz, 1H), 7.69 (d, J = 7.5 Hz, 1H), 7.21 (d, J = 8.7 Hz, 2H), 6.87 (d, J = 8.7 Hz, 2H), 4.76 (s, 2H), 3.80 (s, 3H), 3.15 (d, J = 2.8 Hz, 3H), 2.78 (dd, J = 14.0, 7.1 Hz, 1H), 1.17 (d, J = 6.8 Hz, 6H) |
| 51 | 261 ([M + H]⁺) | 75-76 | white solid | | (300 MHz, CDCl₃) δ 8.51 (s, 1H), 7.95 (d, J = 6.1 Hz, 1H), 7.76 (dd, J = 7.5, 1.9 Hz, 2H), 7.43 (m, 3H), 3.26 (d, J = 2.3 Hz, 6H) |

TABLE II-continued

Characterization Data for the Compounds in Table I

| Compound | ESIMS m/z | mp (° C.) | Appearance | IR (thin film, cm$^{-1}$) | $^1$H NMR (field strength, solvent) |
|---|---|---|---|---|---|
| 52 | 295 ([M + H]$^+$) | 144-146 | white solid | | (300 MHz, CDCl$_3$) δ 8.47 (s, 1H), 7.94 (d, J = 6.0 Hz, 1H), 7.70 (d, J = 8.6 Hz, 2H), 7.40 (d, J = 8.5 Hz, 2H), 3.26 (d, J = 2.3 Hz, 6H) |
| 53 | 291 ([M + H]$^+$) | 106-107 | white solid | | (300 MHz, CDCl3) δ 8.45 (s, 1H), 7.94 (d, J = 6.1 Hz, 1H), 7.70 (d, J = 8.8 Hz, 2H), 6.93 (d, J = 8.9 Hz, 2H), 3.85 (s, 3H), 3.25 (d, J = 2.3 Hz, 6H) |
| 54 | 199 ([M + H]$^+$) | 122-124 | white solid | | (300 MHz, CDCl$_3$) δ 7.89 (m, 2H), 3.23 (d, J = 2.3 Hz, 6H), 2.07 (d, J = 5.9 Hz, 3H) |
| 55 | 227 ([M + H]$^+$) | 90-92 | white solid | | (300 MHz, CDCl$_3$) δ 7.90 (d, J = 6.1 Hz, 1H), 7.69 (d, J = 7.6 Hz, 1H), 3.23 (d, J = 2.3 Hz, 6H), 2.78 (dq, J = 13.7, 7.0 Hz, 1H), 1.17 (d, J = 6.8 Hz, 6H) |

Example 6

TABLE III-continued

One-Day Protectant (1DP) and Three-Day Curative
(3DC) Activity of Compounds on SEPTTR at 100 ppm

| Compound | SEPTTR 100 ppm 1DP | SEPTTR 25 ppm 1DP | SEPTTR 100 ppm 3DC | SEPTTR 25 ppm 3DC |
|---|---|---|---|---|
| 38 | D | D | B | C |
| 39 | E | E | E | E |
| 40 | D | D | B | D |
| 41 | E | E | E | E |
| 42 | C | D | D | D |
| 43 | D | D | C | C |
| 44 | E | E | E | E |
| 45 | D | D | D | C |
| 46 | D | D | A | C |
| 47 | C | C | B | C |
| 48 | D | D | B | C |
| 49 | D | D | C | D |
| 50 | D | D | C | C |
| 51 | D | D | B | D |
| 52 | D | D | C | D |
| 53 | D | D | D | D |
| 54 | D | D | D | D |
| 55 | D | D | D | D |

What is claimed is:

1. A compound of Formula I:

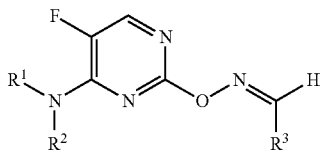

Formula I wherein $R^1$ is:
H;
$C_1$-$C_6$ alkyl optionally substituted with $R^4$;
$C_1$-$C_6$ alkenyl optionally substituted with $R^4$;
$C_3$-$C_6$ alkynyl optionally substituted with $R^4$;
phenyl or benzyl wherein each of the phenyl or the benzyl may be optionally substituted with 1-3 $R^5$, a 5- or 6-membered saturated or unsaturated ring containing 1-3 heteroatoms wherein each ring may be optionally substituted with 1-3 $R^5$;
—$(CHR^6)_m OR^7$;
—$C(=O)R^8$;
—$C(=S)R^8$;
—$C(=O)OR^8$;
—$C(=S)OR^8$;
—$(CHR^6)_m N(R^9)R^{10}$;
—$C(=O)N(R^9)R^{10}$; or
—$C(=S)N(R^9)R^{10}$;

m is an integer from 1 to 3;
$R^2$ is: H; or
$C_1$-$C_6$ alkyl optionally substituted with $R^4$;
alternatively $R^1$ and $R^2$ may be taken together to form:
=$CR^{11}N(R^{12})R^{13}$;
$R^3$ is independently $C_1$-$C_6$ alkyl, $C_1$-$C_6$ cycloalkyl, $C_1$-$C_5$ haloalkyl, $C_2$-$C_6$ alkylcarbonyl, $C_2$-$C_6$ alkylaminocarbonyl, (hetero)arylcarbonyl, (hetero)aryloxycarbonyl, (hetero)arylaminocarbonyl, benzyl, phenyl, or 5- or 6-membered heteroaromatic ring, wherein each (hetero)aryl, phenyl, benzyl, or 5- or 6-membered heteroaromatic ring may be optionally substituted with 1 to 3 substituents independently selected from $R^5$;

$R^4$ is independently halogen, $C_1$-$C_6$ alkyl, $C_1$-$C_4$ haloalkyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_3$ alkylamino, $C_2$-$C_6$ alkoxycarbonyl, $C_2$-$C_6$ alkylcarbonyl, or $C_2$-$C_6$ alkylaminocarbonyl;
$R^5$ is independently halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, amino, $C_1$-$C_6$ alkylamino, $C_2$-$C_6$ dialkylamino, $C_2$-$C_6$ alkoxycarbonyl, or $C_2$-$C_6$ alkylcarbonyl, nitro, or cyano;
$R^6$ is H, $C_1$-$C_6$ alkyl, $C_1$-$C_6$ alkoxy, phenyl or benzyl wherein each of the phenyl or benzyl may be optionally substituted with 1 to 3 substituents independently selected from $R^5$;
$R^7$ is H, $C_1$-$C_6$ alkyl, $C_2$-$C_6$ alkenyl, $C_3$-$C_6$ alkynyl, $C_1$-$C_6$ haloalkyl, $C_1$-$C_6$ alkoxyalkyl, $C_2$-$C_6$ alkylcarbonyl, phenyl or benzyl wherein each of the phenyl or benzyl may be optionally substituted with 1 to 3 $R^5$, or a 5- or 6-membered saturated or unsaturated ring containing 1 to 3 heteroatoms wherein each ring may be optionally substituted with 1 to 3 substituents independently selected from $R^5$;
$R^8$ is H, $C_1$-$C_6$ alkyl, $C_2$-$C_6$ alkenyl, $C_3$-$C_6$ alkynyl, $C_1$-$C_6$ haloalkyl, $C_1$-$C_6$ alkoxyalkyl, phenyl or benzyl wherein each of the phenyl or the benzyl may be optionally substituted with 1 to 3 $R^5$, or a 5- or 6-membered saturated or unsaturated ring containing 1 to 3 heteroatoms wherein each ring may be optionally substituted with 1 to 3 substituents independently selected from $R^5$;
$R^9$ is H, $C_1$-$C_6$ alkyl, $C_1$-$C_6$ haloalkyl, $C_1$-$C_6$ alkoxyalkyl, $C_2$-$C_6$ alkylcarbonyl, phenyl or benzyl wherein each of the phenyl or the benzyl may be optionally substituted with 1-3 $R^5$, or a 5- or 6-membered saturated or unsaturated ring containing 1-3 heteroatoms wherein each ring may be optionally substituted with 1-3 $R^5$;
$R^{10}$ is H, $C_1$-$C_6$ alkyl, $C_1$-$C_6$ haloalkyl, $C_1$-$C_6$ alkoxyalkyl, $C_2$-$C_6$ alkylcarbonyl, benzyl, wherein the benzyl may be optionally substituted with 1-3 $R^5$
alternatively $R^9$ and $R^{10}$ may be taken together to form:
a 5- or 6-membered saturated or unsaturated ring containing 1-3 heteroatoms wherein each ring may be optionally substituted with 1-3 $R^5$;
$R^{11}$ is H or $C_1$-$C_4$ alkyl;
$R^{12}$ is H, $C_1$-$C_4$ alkyl, $C_1$-$C_6$ alkoxy, $C_2$-$C_6$, alkylcarbonyl, phenyl or benzyl wherein each of the phenyl or the benzyl may be optionally substituted with 1-3 $R^5$;
alternatively $R^{11}$ and $R^{12}$ may be taken together to form:
a 5- or 6-membered saturated or unsaturated ring containing 1-3 heteroatoms wherein each ring may be optionally substituted with 1-3 $R^5$;
$R^{13}$ is H, $C_1$-$C_4$ alkyl, $C_1$-$C_6$ alkoxy, $C_2$-$C_6$, alkylcarbonyl, phenyl or benzyl wherein each of the phenyl or the benzyl may be optionally substituted with 1-3 $R^5$;
alternatively $R^{12}$ and $R^{13}$ may be taken together to form:
a 5- or 6-membered saturated or unsaturated ring containing 1-3 heteroatoms wherein each ring may be optionally substituted with 1-3 $R^5$.

2. A composition for the control of a fungal pathogen including the compound of claim 1 and a phytologically acceptable carrier material.

3. The composition of claim 2 wherein the fungal pathogen is Apple Scab (*Venturia inaequalis*), Leaf Blotch of Wheat (*Septoria tritici*), Leaf Spot of Sugarbeets (*Cercospora beticola*), Leaf Spots of Peanut (*Cercospora arachidicola*), and Black Sigatoka of Banana (*Mycosphaerella fijiensis*).

4. A method for the control of fungal attack on a plant, the method including the steps of:
applying a fungicidally effective amount of at least one of the compounds of claim 1 to at least one of the plant, an area adjacent to the plant, soil adapted to support growth of the plant, a root of the plant, foliage of the plant, and a seed adapted to produce the plant.

5. The compound of claim 1, wherein the compound is:
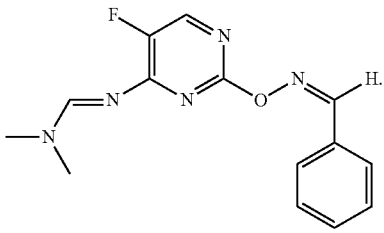
6. The compound of claim 1, wherein the compound is:
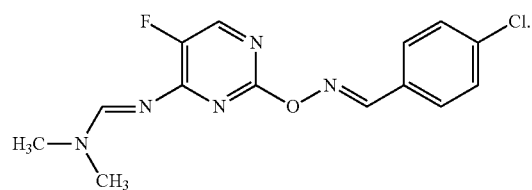 [SMILES: CN(C)/C=N/c1nc(O/N=C/c2ccc(Cl)cc2)ncc1F]
7. The compound of claim 1, wherein the compound is:
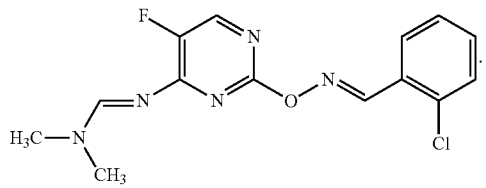 [SMILES: CN(C)/C=N/c1nc(O/N=C/c2ccccc2Cl)ncc1F]
8. The compound of claim 1, wherein the compound is:
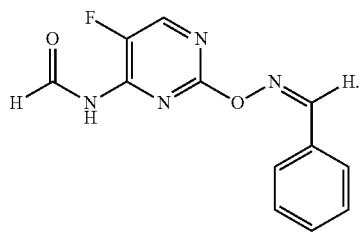
9. The compound of claim 1, wherein the compound is:
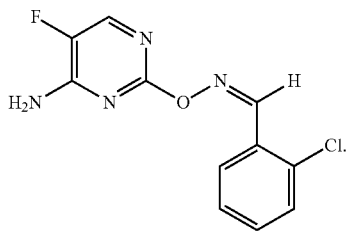 [SMILES: Nc1nc(O/N=C\c2ccccc2Cl)ncc1F]
10. The compound of claim 1, wherein the compound is:
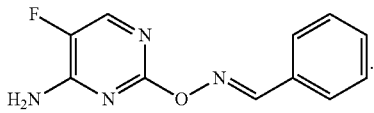 [SMILES: Nc1nc(O/N=C/c2ccccc2)ncc1F]
* * * * *